(12) United States Patent
Blagg et al.

(10) Patent No.: US 8,188,306 B2
(45) Date of Patent: May 29, 2012

(54) HEAT SHOCK PROTEIN 90 INHIBITORS

(75) Inventors: Brian S. J. Blagg, Lawrence, KS (US); Gang Shen, Ballwin, MO (US)

(73) Assignee: University of Kansas, Lawrence, KS (US)

( * ) Notice: Subject to any disclaimer, the term of this patent is extended or adjusted under 35 U.S.C. 154(b) by 141 days.

(21) Appl. No.: 12/570,804

(22) Filed: Sep. 30, 2009

(65) Prior Publication Data

US 2010/0099865 A1    Apr. 22, 2010

Related U.S. Application Data

(62) Division of application No. 11/728,393, filed on Mar. 26, 2007, now Pat. No. 7,605,288, which is a division of application No. 10/976,082, filed on Oct. 27, 2004, now Pat. No. 7,208,630.

(51) Int. Cl.
| | | |
|---|---|---|
| C07C 233/02 | (2006.01) | |
| C07C 233/11 | (2006.01) | |
| C07C 69/00 | (2006.01) | |
| C07D 223/00 | (2006.01) | |
| C07D 487/00 | (2006.01) | |

(52) U.S. Cl. .......... 560/9; 560/11; 560/19; 560/51; 560/64; 560/65; 560/118; 564/123; 564/161; 564/163; 564/169; 564/171; 540/203; 540/476; 540/479; 540/484; 540/546

(58) Field of Classification Search .................. None
See application file for complete search history.

(56) References Cited

U.S. PATENT DOCUMENTS

| | | |
|---|---|---|
| 6,046,239 A | 4/2000 | Lennox et al. |
| 7,208,630 B2 | 4/2007 | Blagg et al. |
| 7,605,288 B2 | 10/2009 | Blagg et al. |

OTHER PUBLICATIONS

"The Design, Synthesis, and Biological Evaluation of Chimera Based Inhibitors of Hsp90, A Novel Approach to Cancer Chemotherapeutics" Poster presentation at Annual Chemical Society meeting in New York on Sep. 8, 2003.
Roe et al. (1999) J. Med. Chem.42:260-266 "Structural Basis for Inhibition of the Hsp90 Molecular Chaperone by the Antitumor Antibiotics Radicicol and Geldanamycin".
Shen et al., "Design, synthesis, and structure-activity relationships for chimeric inhibitors of Hsp90", J. Org. Chem. 2006, 71, 7618-7631. Aug. 31, 2006.
Shen and Blagg, Radester, a novel inhibitor of the Hsp90 protein folding machinery, Org. Lett. 2005, 7(11): 2157-2160. May 3, 2005.
Clevenger and Blagg, "Design, synthesis and evaluation of a radicol and geldanamycin chimera, radamide", Org. let. 2004, 6 (24): 4459-4462.Oct. 30, 2004.
Hadden and Blagg, "Synthesis and evaluation of radamide analogues, a chimera of radical and geldanamycin". J. Org. Chem., 2009, 74, 4697-4704. Jun. 3, 2009.

*Primary Examiner* — Yevegeny Valenrod
(74) *Attorney, Agent, or Firm* — Merchant & Gould P.C.

(57) ABSTRACT

Novel compounds useful for inhibiting the 90kDa heat shock proteins containing a quinone-like moiety and a di-hydroxy phenol like moiety, similar to geldanamycin and radicicol.

9 Claims, 5 Drawing Sheets

HEAT SHOCK PROTEIN 90 INHIBITORS

CROSS-REFERENCE TO RELATED APPLICATIONS

This is a divisional application of U.S. patent application Ser. No. 11/728,393, filed on Mar. 26, 2007, which is a divisional application of U.S. patent application Ser. No. 10/976,082, filed on Oct. 27, 2004, now U.S. Pat. No. 7,208,630, each of which is incorporated herein by reference in its entirety.

STATEMENT REGARDING FEDERALLY SPONSORED RESEARCH OR DEVELOPMENT

The present invention was sponsored by the National Institute of Health Contract No. COBRE RR017708, and the government may have certain rights in the invention.

BACKGROUND OF THE INVENTION

1. Field of the Invention

The present invention is directed to novel compounds useful as inhibitors of heat shock 90 proteins ("Hsp90"), the molecular chaperones responsible for protein folding and maturation in vivo and which have been found at higher levels in cancerous cells than in normal cells. The compounds of the present invention have a chimeric structure based, in part, on two naturally occurring Hsp90 inhibitors: radicicol ("RDC") and geldanamycin ("GDA").

2. Description of Related Art

The 90 kDa heat shock proteins belong to a family of chaperones that regulate intracellular functions and are required for the refolding of denatured proteins following heat shock, as well as the conformational maturation of a large number of key proteins involved in cellular processes. The Hsp90 family of chaperones is comprised of four different isoforms. Hsp90 α and Hsp90 β are found predominately in the cytosol, the 94-kDa glucose-regulated protein ("GRP94") is localized to the endoplasmic reticulum, and Hsp75/tumour necrosis factor receptor associated protein 1 ("TRAP-1") resides mainly in the mitochondrial matrix. These Hsp90s bind to client proteins in the presence of cochaperones, immunophilins, and partner proteins to make the multiprotein complex responsible for conformational maturation of newly formed nascent peptides into biologically active three-dimensional structures.

As discussed more fully below, Hsp90 is an ATP-dependent protein with an ATP binding site in the N-terminal region of the active homodimer. Disruption of the ATPase activity of Hsp90 results in the destabilization of multiprotein complexes and subsequent ubiquitination of the client protein, which undergoes proteasome-mediated hydrolysis. More specifically, in an ATP-dependent fashion, Hsp70 binds to newly synthesized proteins cotranslationally and/or post-translationally to stabilize the nascent peptide by preventing aggregation. Stabilization of the Hsp70/polypeptide binary complex is dependent upon the binding of Hsp70 interacting protein ("HIP"), which occurs after Hsp70 binds to the newly formed peptide. Hsp70-Hsp90 organizing protein ("HOP") contains highly conserved tetratricopeptide repeats ("TPRs") that are recognized by both Hsp70 and Hsp90, promoting the union of Hsp70/HIP and Hsp90, which results in a heteroprotein complex. In the case of telomerase and steroid hormone receptors, the client protein is transferred from the Hsp70 system to the Hsp90 homodimer with concomitant release of Hsp70, HIP, and HOP. Upon binding of ATP and an immunophilin with cis/trans peptidyl prolyl-isomerase activity (FKBP51, FKBP52, or CyPA), the ensemble folds the client protein into its three-dimensional structure. In a subsequent event, p23 binds Hsp90 near the N-terminal region promoting the hydrolysis of ATP and release of the folded protein, Hsp90 partner proteins, and ADP.

Examples of proteins dependent upon Hsp90 for conformational maturation include oncogenic Src kinase, Raf, p185, mutant p53 (not normal p53), telomerase, steroid hormone receptors, polo-like kinase ("PLK"), protein kinase B ("AKT"), death domain kinase ("RIP"), MET kinase, focal adhesion kinase ("FAK"), aryl hydrocarbon receptor, RNA-dependent protein kinase ("PKR"), nitric oxide synthase ("NOS"), centrosomal proteins, and others. In addition, other proteins, such as cyclin dependent kinase 4 ("CDK4"), cyclin dependent kinase 6 ("CDK6"), and human epidermal growth factor receptor 2 ("Her-2") are thought to be client proteins of Hsp90. Of these Hsp90 client proteins, Raf, PLK, RIP, AKT, FAK, telomerase, and MET kinase are directly associated with the six hallmarks of cancer: (1) self-sufficiency in growth signals; (2) insensitivity to antigrowth signals; (3) evasion of apoptosis; (4) unlimited replication potential; (5) sustained angiogenesis; and (6) tissue invasion/metastasis. Consequently, Hsp90 is a target for the development of cancer therapeutics because multiple signaling pathways can be simultaneously inhibited by disruption of the Hsp90 protein folding machinery.

Known inhibitors of Hsp90 include the anti-tumor antibiotics geldanamycin ("GDA"), radicicol ("RDC"), herbimycin A ("HB"), a 17-allylamino derivative of GDA ("17-AAG"), and the synthetic ATP analog called PU3. The structures of these prior art Hsp90 inhibitors are shown in FIG. 1.

These prior art molecules exert their activity by binding to the N-terminal ATP binding pocket and inhibit the ATPase activity of Hsp90. The energy normally derived from ATP hydrolysis is used to elicit a conformational change that releases the properly folded client protein from Hsp90. However, when a non-hydrolyzable inhibitor is present, Hsp90 is unable to fold the bound client protein, resulting in ubiquitination of the client protein and subsequent proteolysis by the proteasome.

As shown in FIG. 2, when the co-crystal structures of GDA and RDC were solved, it was determined the quinone ring of GDA and the 2,4-diphenol of RDC bound in opposite orientations. See Roe et al., *Structural Basis for Inhibition of the Hsp90 Molecular Chaperone by the Antitumor Antibiotics Radicicol and Geldanamycin*, J. Med. Chem. 1999, 42, 260-266, which is incorporated by reference in its entirety. The 2,4-dihydroxy moiety of RDC binds in the same location as the adenine ring of ADP and mimics the hydrogen bond donor/acceptor properties of the exo- and N7 endocyclic amines. The quinone ring of GDA binds towards the exterior of the pocket and facilitates hydrogen bond interactions with the diphosphate-binding region. The $K_d$ of GDA and RDC is estimated to be about 1200 and 19 nM, respectively.

Several Hsp90 inhibitors have been investigated therapeutically. GDA has potent activity in vitro with an $IC_{50}$ of 1-3 μm. However, in vivo GDA has a greater affinity for the Hsp90 complex with an $IC_{50}$ of 100 nM. As a result, a derivative of GDA, 17-AAG, has entered Phase I clinical trials for the treatment of several cancers.

Several modifications to the GDA and RDC structures have also been investigated therapeutically to some extent. For example, based on bovine Hsp90, researchers have suggested that removal of the C28 methyl substituent of GDA or incorporation of an H-bond donor into this position would lead to increased affinity. See Stebbins et al., *Crystal Structure of*

Hsp90-*Geldanamycin Complex: Targeting of a Protein Chaperone by an Antitumor Agent*, Cell, 1997, 89, 239-250, which is incorporated by reference in its entirety. Modifications of the quinone moiety of GDA have demonstrated that replacement of the C17 methyl ether with amino side chains enhanced the biological activity as evidenced by lower IC50s via stabilization of the quinone ring and the conservation of a hydrogen bond acceptor at this position. See Schnur et al., *Inhibition of the Oncogene Product p185erb-2 in Vitro and in Vivo by Geldanamycin and Dihydrogeldanamycin Derivatives*, J. Med. Chem. 1995, 38, 3806-3812; Schnur et al., *erB-2 Oncogene Inhibition by Geldanamycin Derivatives: Synthesis, Mechanism of Action, and Structure-Activity Relationships*, J. Med. Chem. 1995, 38, 3813-3820; Sasaki et al., *Growth Inhibition of Virus Transformed Cells In Vitro and Antitumor Activity In Vivo of Geldanamycin and Its Derivatives*, J. Antibiotics 1979, 32, 849-854, which are all incorporated by reference in their entirety. In addition, when the co-crystal structure of Hsp90 bound to GDA was solved, the authors suggested the meta-carbonyl was acting as a hydrogen bond acceptor. See Roe et al., *Structural Basis for Inhibition of the Hsp90 Molecular Chaperone by the Antitumor Antibiotics Radicicol and Geldanamycin*, J. Med. Chem. 1999, 42, 260-266, which is incorporated by reference in its entirety. Also, Santi and coworkers have recently reported the co-crystal structure of 17-dimethylaminoethylamino-geldanamycin (DMAG) bound to Hsp90 and performed a series of computational studies to understand the relationship between the bent conformation of GDA found in the Hsp90 binding site and its native conformation. See Jez et al., *Crystal structure and molecular modeling of 17-DMAG in complex with human Hsp90*, Chem. Biol. 2003, 10, 361-368, which is incorporated by reference in its entirety. Their studies suggest that GDA binds to Hsp90, and is twisted into a bent conformation by isomerization of the amide bond (trans→cis), which results in an enthalpic penalty between 2.2 and 6.4 kcal/mol. They further suggested that analogues of GDA that contain a cis-amide will have >1000 fold increase in affinity for Hsp90.

Although GDA and RDC have been shown to inhibit Hsp90 and some GDA and RDC derivatives have been proposed, there remains a need to develop other Hsp90 inhibitors as useful anti-cancer agents. Most preferably, these new Hsp90 inhibitors have decreased toxicity, increased solubility, and/or increased selectivity for Hsp90.

The present invention is directed to novel compounds having a chimeric structure comprised of moieties that mimic the binding regions of the prior art Hsp90 inhibitors. Most preferably, the novel compounds contain moieties that mimic the interactions of both GDA and RDC with Hsp90. These novel Hsp90 inhibitors bind to the N-terminal ATP binding region of Hsp90, and have a predicted $K_d$ in the submicromolar range (even in the nanomolar and picomolar range). Furthermore, the present invention also includes modified derivatives and analogues of the chimeric compounds. These derivatives include the seco-ester and seco-amide variations of the chimeric structure.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

SUMMARY OF THE INVENTION

It is an object of the present invention is to provide compounds having the following Formula I:

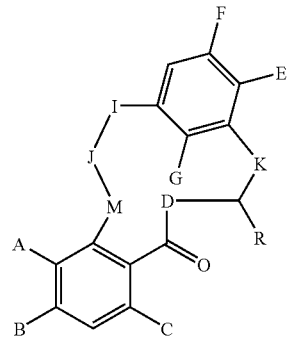

wherein A is hydrogen, halogen, lower alkyl, lower alkoxy, aryl, aralyl, allyl, or together with B and the atoms to which they are attached form a heterocyclic ring having 4 to 12 ring members with at least one heteroatom selected from oxygen, nitrogen, or sulfur;

wherein B is hydroxy, amino, halogen, lower alkoxy, aralkoxy, or together with A and the atoms to which they are attached form a heterocyclic ring having 4 to 12 ring members with at least one heteroatom selected from oxygen, nitrogen, or sulfur;

wherein C is hydroxy, amino, or lower alkoxy;

wherein D is alkyl, oxygen, amino, sulfanyl, sulfenyl, or sulfonyl;

wherein E is halogen, hydroxy, lower alkoxy, amino, allyl amine, or together with F and the atoms to which they are attached form a heterocyclic ring having 4 to 12 ring members with at least one heteroatom selected from oxygen, nitrogen, or sulfur;

wherein F is hydroxy, halogen, thiol, lower alkoxy, amino, oxidized to form a ketone, or together with E and the atoms to which they are attached form a heterocyclic ring having 4 to 12 ring members with at least one heteroatom selected from oxygen, nitrogen, or sulfur;

wherein G is hydrogen, halogen, amino, thiol, hydroxy, lower alkyl, lower alkoxy, or oxidized to form a ketone;

wherein I is amino, alkyl, carbonyl, sulfanyl, sulfenyl, sulfonyl, or oxygen;

wherein J is alkyl, amino, carbonyl, sulfanyl, sulfenyl, sulfonyl, or oxygen;

wherein M is alkyl or cycloalkyl;

wherein K is alkyl or cycloalkyl; and wherein R is hydrogen or alkyl.

In another aspect, the present invention is directed to compounds according to Formula I wherein A is halogen; wherein B and C are both hydroxy; wherein D is oxygen; wherein E is lower alkoxy; wherein F and G are both oxidized to form a quinone; wherein K is alkyl; wherein I is amino comprising —NH—; wherein J is carbonyl; wherein M is lower alkyl; wherein R is hydrogen or alkyl.

In still another aspect of the present invention, compounds according to Formula I are provided wherein A is halogen; wherein B and C are both hydroxy; wherein D is oxygen; wherein E is lower alkoxy; wherein F and G are both hydroxy; wherein I is amino comprising —NH—; wherein J is carbonyl; wherein K is alkyl; wherein M is lower alkyl; and wherein R is hydrogen or alkyl.

In another aspect, the present invention is directed to compounds of Formula I wherein A is halogen; wherein B and C are both hydroxy; wherein D is oxygen; wherein E, F, and G are all lower alkoxy; wherein I is amino comprising —NH—; wherein J is carbonyl; wherein K is alkyl; wherein M is lower alkyl; and wherein R is hydrogen or alkyl.

In yet another aspect, compounds of Formula I are provided wherein A is halogen; wherein B and C are both hydroxy; wherein D is oxygen; wherein E is allyl amine; wherein F and G are both oxidized to form a quinone; wherein I is amino comprising —NH—; wherein J is carbonyl, wherein K is alkyl; wherein M is lower alkyl; and wherein R is hydrogen or alkyl.

In still another aspect, compounds according to Formula I are provided wherein A is phenyl; wherein B and C are both hydroxy; wherein D is oxygen; wherein E, F, and G are all lower alkoxy; wherein I is amino comprising —NH—; wherein J is carbonyl; wherein K is alkyl; wherein M is lower alkyl; and wherein R is hydrogen or alkyl.

In yet another aspect, the present invention is directed to compounds according to Formula I wherein A is halogen; wherein B is lower alkoxy; wherein C is hydroxy; wherein D is oxygen; wherein E, F, and G are all lower alkoxy; wherein I is amino comprising —NH—; wherein J is carbonyl; wherein K is alkyl; wherein M is lower alkyl; and wherein R is hydrogen or alkyl.

In a further aspect, the present invention is directed to compounds according to Formula I wherein A is halogen; wherein B and C are both hydroxy; wherein D is oxygen; wherein E, F, and G are all lower alkoxy; wherein I is amino comprising the formula —NR$_1$— and wherein R$_1$ is alkyl; wherein J is carbonyl; wherein K is alkyl; wherein M is lower alkyl; and wherein R is hydrogen or alkyl.

In still another aspect, the present invention is directed to compounds according to Formula I wherein A is halogen; wherein B and C are both hydroxy; wherein D is oxygen; wherein E, F, and G are all lower alkoxy; wherein I is amino comprising —NH—; wherein J is carbonyl; wherein K is lower alkyl; wherein M is lower alkyl; and wherein R is hydrogen or alkyl.

In yet another aspect, the present invention is directed to compounds of Formula I wherein both G and F are oxidized to form a quinone.

In yet another aspect, the present invention is directed to compounds of Formula I wherein B and C are both hydroxy.

In yet another aspect, the present invention is directed to compounds of Formula I wherein A is halogen.

In yet another aspect, the present invention is directed to compounds of Formula I wherein R is hydrogen.

In yet another aspect, the present invention is directed to compounds of Formula I wherein G and F are both hydroxy.

In yet another aspect, the present invention is directed to compounds of Formula I wherein E, F, and G are each lower alkoxy.

In yet another aspect, the present invention is directed to compounds of Formula I wherein F and G are oxidized to form a quinone, and E is allyl amine.

In still another aspect, the present invention is directed to compounds of the Formula II:

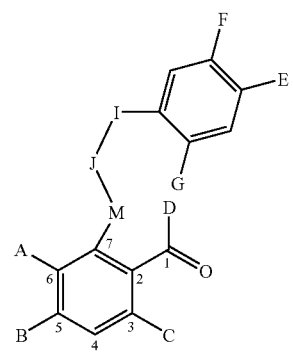

wherein A is hydrogen, halogen, lower alkyl, lower alkoxy, aryl, aralyl, allyl, or together with B and the atoms to which they are attached form a heterocyclic ring having 4 to 12 ring members with at least one heteroatom selected from oxygen, nitrogen, or sulfur;

wherein B is hydroxy, amino, halogen, lower alkoxy, aralkoxy, or together with A and the atoms to which they are attached form a heterocyclic ring having 4 to 12 ring members with at least one heteroatom selected from oxygen, nitrogen, or sulfur;

wherein C is hydroxy, amino, or lower alkoxy;

wherein D is hydroxy, lower alkyl, lower alkoxy, amino, or together with M and the carbon atoms to which they are attached and the carbon at position 2 form a carbocyclic ring having 5 to 8 ring members;

wherein E is hydroxy, halogen, lower alkoxy, amino, allyl amine, or together with F and the atoms to which they are attached form a heterocyclic ring having 4 to 12 ring members with at least one heteroatom selected from oxygen, nitrogen, or sulfur;

wherein F is hydroxy, halogen, thiol, lower alkoxy, amino, oxidized to form a ketone, or together with E and the atoms to which they are attached form a heterocyclic ring having 4 to 12 ring members with at least one heteroatom selected from oxygen, nitrogen, or sulfur;

wherein G is hydrogen, halogen, amino, thiol, hydroxy, lower alkyl, lower alkoxy, oxidized to form a ketone, or together with I, J, and M, and the carbon atoms to which G and I are attached form a heterocycle ring having 5 to 8 ring members with at least one heteroatom selected from oxygen, nitrogen, or sulfur;

wherein I is alkyl, amino, carbonyl, sulfanyl, sulfenyl, sulfonyl, oxygen, or together with G, J, and M, and the carbon atoms to which G and I are attached form a heterocycle ring having 5 to 8 ring members with at least one heteroatom selected from oxygen, nitrogen, or sulfur;

wherein J is alkyl, amino, carbonyl, sulfanyl, sulfenyl, sulfonyl, oxygen, or together with I, M, and G, and the carbon atoms to which G and I are attached form a heterocycle ring having 5 to 8 ring members with at least one heteroatom selected from oxygen, nitrogen, or sulfur; and wherein M is alkyl, cycloalkyl; or M together with I, J, and G and the carbons to which G and I are attached form a heterocycle ring having 5 to 8 ring members with at least one heteroatom selected from oxygen, nitrogen, or sulfur; or M together with D and the carbon atoms to which they are attached form a heterocylic ring having 4 to 12 ring members with at least one heteroatom selected from oxygen, nitrogen, and sulfur; or M is alkyl and together with I, J, and G and the carbons to which G and I are attached form a heterocycle ring having 5 to 8 ring members with at least one heteroatom selected from oxygen, nitrogen, or sulfur; or M is alkyl and together with D and the carbon atoms to which they are attached form a heterocylic ring having 4 to 12 ring members with at least one heteroatom selected from oxygen, nitrogen, and sulfur.

In yet another aspect, compounds according Formula II(B) are provided:

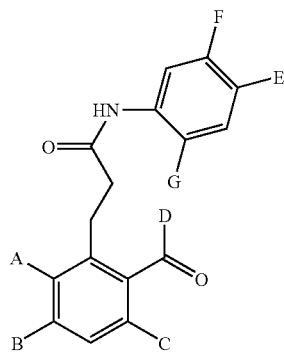

wherein A is hydrogen, chlorine, fluorine, methyl, phenyl, benzyl, or allyl;

wherein B is hydroxy, chlorine, fluorine, methoxy, ethoxy, or benzyloxy;

wherein C is hydroxy, methoxy, or amino comprising —NH$_2$;

wherein D is hydroxy, methoxy, ethoxy, or amino comprising —NH$_2$, —NHCH$_3$, or —N(CH$_3$)$_2$;

wherein E is hydroxy, chlorine, fluorine, methoxy, ethoxy, amino comprising —NH$_2$, or allyl amine comprising —NHCHCH=CH$_2$;

wherein F is hydroxy, chlorine, fluorine, methoxy, ethoxy, amino, thiol, or is oxidized to form a ketone; and wherein G is hydrogen, hydroxy, methyl, methoxy, ethoxy, or is oxidized to form a ketone.

In yet another aspect, compounds according to Formula II(C) are provided:

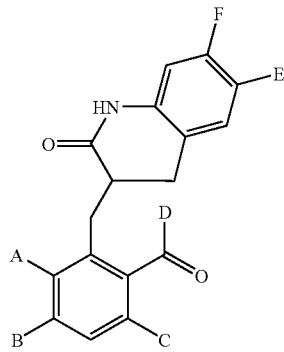

wherein A is hydrogen, chlorine, fluorine, methyl, phenyl, benzyl, or allyl;

wherein B is hydroxy, chlorine, fluorine, methoxy, ethoxy, or benzyloxy;

wherein C is hydroxy, methoxy, ethoxy, or amino comprising —NH$_2$;

wherein D is hydroxy, methoxy, ethoxy, or amino comprising —NH$_2$, —NHCH$_3$, or —N(CH$_3$)$_2$;

wherein E is hydroxy, chlorine, fluorine, methoxy, ethoxy, amino comprising —NH$_2$, or allyl amine comprising —NHCHCH=CH$_2$; and wherein F is hydroxy, chlorine, fluorine, methoxy, ethoxy, amino comprising —NH$_2$, thiol, or is oxidized to form a ketone.

In still a further aspect, the present invention is directed to compounds of Formula Formula II(D):

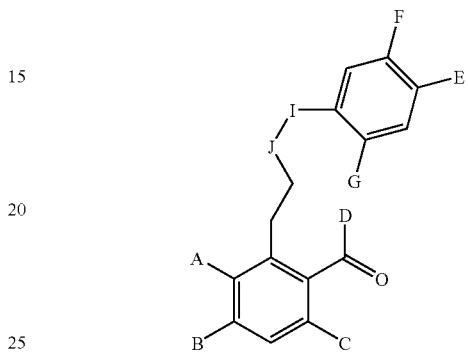

wherein A is hydrogen, chlorine, fluorine, methyl, phenyl, benzyl, or allyl;

wherein B is hydroxy, chlorine, fluorine, methoxy, ethoxy, or benzyloxy;

wherein C is hydroxy, methoxy, ethoxy, or amino comprising —NH$_2$;

wherein D is hydroxy, methoxy, ethoxy, or amino comprising —NH$_2$, —NHCH$_3$, or —N(CH$_3$)$_2$;

wherein E is hydroxy, chlorine, fluorine, methoxy, ethoxy, amino comprising —NH$_2$, or allyl amine comprising —NHCHCH=CH$_2$;

wherein F is hydroxy, chlorine, fluorine, methoxy, ethoxy, amino, thiol, or is oxidized to form a ketone;

wherein G is hydrogen, hydroxy, methyl, methoxy, ethoxy, or is oxidized to form a ketone;

wherein I is amino comprising —NH— or —NCH$_3$—, lower alkyl comprising —CH$_2$—, carbonyl, sulfanyl, or oxygen; and wherein J is carbonyl, amino, lower alkyl, sulfanyl, or oxygen.

In yet another aspect, compounds according Formula II(E) are provided:

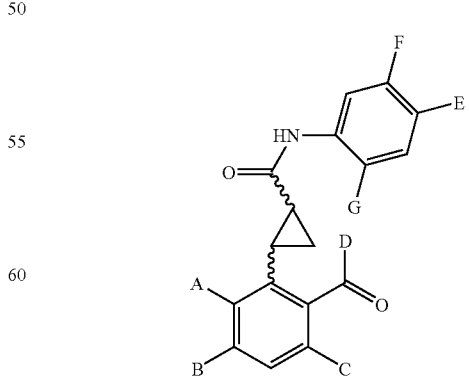

wherein A is hydrogen, chlorine, fluorine, methyl, phenyl, benzyl, or allyl;

wherein B is hydroxy, chlorine, fluorine, methoxy, ethoxy, or benzyloxy;

wherein C is hydroxy, methoxy, ethoxy, or amino comprising —NH$_2$;

wherein D is hydroxy, methoxy, ethoxy, or amino comprising —NH$_2$, —NHCH$_3$, or —N(CH$_3$)$_2$;

wherein E is hydroxy, chlorine, fluorine, methoxy, ethoxy, amino comprising —NH$_2$, or allyl amine comprising —NHCHCH=CH$_2$;

wherein F is hydroxy, chlorine, fluorine, methoxy, ethoxy, amino, thiol, or is oxidized to form a ketone; and wherein G is hydrogen, hydroxy, methyl, methoxy, ethoxy, or oxidized to form a ketone.

In still another aspect, the compounds according to Formula II(F) are provided:

[Structure of Formula II(F)]

wherein A is hydrogen, chlorine, fluorine, methyl, phenyl, benzyl, or allyl;

wherein B is hydroxy, chlorine, fluorine, methoxy, ethoxy, or benzyloxy;

wherein C is hydroxy, methoxy, ethoxy, or amino comprising —NH$_2$;

wherein D is hydroxy, methoxy, ethoxy, or amino comprising —NH$_2$, —NHCH$_3$, or —N(CH$_3$)$_2$;

wherein E and F together with the atoms to which they are attached together form a heterocyclic ring having 5 to 10 ring members with at least one heteroatom selected from oxygen, nitrogen, or sulfur; and wherein G is hydrogen, hydroxy, methyl, methoxy, or ethoxy.

In still a further aspect of the present invention, the compounds according to Formula II(G) are provided:

[Structure of Formula II(G)]

wherein A and B together with the atoms to which they are attached together form a heterocyclic ring having 4 to 10 members with at least one heteroatom selected from oxygen, nitrogen, or sulfur;

wherein C is hydroxy, methoxy, ethoxy, or —NH$_2$;

wherein D is hydroxy, methoxy, ethoxy, —NH$_2$, —NHCH$_3$, or —N(CH$_3$)$_2$;

wherein E is hydroxy, chlorine, fluorine, methoxy, ethoxy, —NH$_2$, or —NHCHCH=CH$_2$;

wherein F is hydroxy, chlorine, fluorine, methoxy, ethoxy, —NH$_2$, thiol, or is oxidized to form a ketone; and wherein G is hydrogen, hydroxy, methyl, methoxy, ethoxy, or is oxidized to form a ketone.

In yet another aspect, compounds according to Formula II are provided wherein wherein A is hydrogen, chlorine, fluorine, methyl, phenyl, benzyl, or allyl; wherein B is hydroxy, chlorine, fluorine, methoxy, ethoxy, or benzyloxy; wherein C is hydroxy, methoxy, ethoxy, or —NH$_2$; wherein D and M together with the carbon atoms to which they are attached and the carbon at position 2 form a carbocyclic ring having 5 to 8 ring members; or M is alkyl and M together with D and the carbon atoms to which they are attached form a heterocylic ring having 4 to 12 ring members with at least one heteroatom selected from oxygen, nitrogen, and sulfur; wherein E is hydroxy, chlorine, fluorine, methoxy, ethoxy, —NH$_2$, or —NHCHCH=CH$_2$; wherein F is hydroxy, chlorine, fluorine, methoxy, ethoxy, —NH$_2$, thiol, or is oxidized to form a ketone; and wherein G is hydrogen, hydroxy, methyl, methoxy, ethoxy or is oxidized to form a ketone.

In still another aspect of the present invention, compounds Formulas II(H) or II(I) below are provided:

FORMULA II (H)

[Structure of Formula II(H)]

FORMULA II (I)

[Structure of Formula II(I)]

wherein A, B, C, D, E, F, and G are defined as set forth in Formula II.

In another aspect, the present invention is directed to compounds according to Formula II wherein A is halogen; wherein B and C are both hydroxy; wherein D is hydroxy, lower alkyl, lower alkoxy, or amino; wherein E is lower alkoxy; wherein F and G are both oxidized to form a quinone, and M is lower alkyl.

In still another aspect of the present invention, compounds according to Formula II are provided wherein A is halogen; wherein B and C are both hydroxy; wherein D is hydroxy, lower alkyl, lower alkoxy, or amino; wherein E is lower alkoxy; wherein F and G are both hydroxy; wherein I is amino comprising —NH—; wherein J is carbonyl; and wherein M is lower alkyl.

In another aspect, the present invention is directed to compounds of Formula II wherein A is halogen; wherein B and C are both hydroxy; wherein D is hydroxy, lower alkyl, lower alkoxy, or amino; wherein E, F, and G are all lower alkoxy; wherein I is amino comprising —NH—; wherein J is carbonyl; and wherein M is lower alkyl.

In yet another aspect, compounds of Formula II are provided wherein A is halogen; wherein B and C are both hydroxy; wherein D is hydroxy, lower alkyl, lower alkoxy, or amino; wherein E is allyl amine; wherein F and G are both oxidized to form a quinone; wherein I is amino comprising —NH—; wherein J is carbonyl, and wherein M is lower alkyl.

In still another aspect, compounds according to Formula II are provided wherein A is phenyl; wherein B and C are both hydroxy; wherein D is hydroxy, lower alkyl, lower alkoxy, or amino; wherein E, F, and G are all lower alkoxy; wherein I is amino comprising —NH—; wherein J is carbonyl; and wherein M is lower alkyl.

In yet another aspect, the present invention is directed to compounds according to Formula II wherein A is halogen; wherein B is lower alkoxy; wherein C is hydroxy; wherein D is hydroxy, lower alkyl, lower alkoxy, or amino; wherein E, F, and G are all lower alkoxy; wherein I is amino comprising —NH—; wherein J is carbonyl; and wherein M is lower alkyl.

In a further aspect, the present invention is directed to compounds according to Formula II wherein A is halogen; wherein B and C are both hydroxy; wherein D is hydroxy, lower alkyl, lower alkoxy, or amino; wherein E, F, and G are all lower alkoxy; wherein I is amino comprising the formula —NR$_1$— and wherein R$_1$ is alkyl; wherein J is carbonyl; and wherein M is lower alkyl.

In still another aspect, the present invention is directed to compounds according to Formula II wherein A is halogen; wherein B and C are both hydroxy; wherein D is hydroxy, lower alkyl, lower alkoxy, or amino; wherein E, F, and G are all lower alkoxy; wherein I is amino comprising —NH—; wherein J is carbonyl; and wherein M is lower alkyl.

In yet another aspect, the present invention is directed to compounds of Formula II wherein both G and F are oxidized to form a quinone.

In yet another aspect, the present invention is directed to compounds of Formula II wherein B and C are both hydroxy.

In yet another aspect, the present invention is directed to compounds of Formula II wherein A is halogen.

In yet another aspect, the present invention is directed to compounds of Formula II wherein G and F are both hydroxy.

In yet another aspect, the present invention is directed to compounds of Formula II wherein E, F, and G are each lower alkoxy.

In yet another aspect, the present invention is directed to compounds of Formula II wherein F and G are oxidized to form a quinone, and E is allyl amine.

In still a further aspect of the present invention, compounds of Formula III are provided:

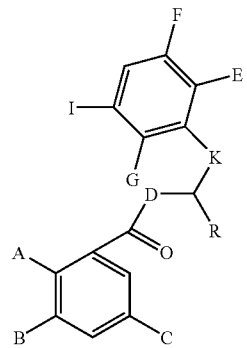

wherein A is hydrogen, halogen, lower alkyl, lower alkoxy, aryl, aralyl, allyl, or together with B and the atoms to which they are attached together form a heterocyclic ring having 4 to 12 ring members with at least one heteroatom selected from oxygen, nitrogen, or sulfur;

wherein B is hydroxy, amino, halogen, lower alkoxy, aralkoxy, or together with A and the atoms to which they are attached together form a heterocyclic ring having 4 to 12 ring members with at least one heteroatom selected from oxygen, nitrogen, or sulfur.

wherein C is hydroxy, amino, or lower alkoxy;

wherein D is alkyl, amino, oxygen, sulfanyl, sulfenyl, sulfonyl, or together with G and K and the carbon atoms to which they are attached form a carbocyclic ring or heterocyclic ring having 5 to 8 ring members; or D is alkyl and together with G and K and the carbon atoms to which they are attached form a carbocyclic ring or heterocyclic ring having 5 to 8 ring members;

wherein E is hydroxy, halogen, lower alkoxy, amino, allyl amine, or together with F and the atoms to which they are attached together form a heterocyclic ring having 4 to 12 ring members with at least one heteroatom selected from oxygen, nitrogen, or sulfur;

wherein F is hydroxy, halogen, thiol, lower alkoxy, amino, is oxidized to form a ketone, or together with E and the atoms to which they are attached together form a heterocyclic ring having 4 to 12 ring members with at least one heteroatom selected from oxygen, nitrogen, or sulfur;

wherein G is hydrogen, hydroxy, halogen, amino, thiol, lower alkyl, lower alkoxy, is oxidized to form a ketone, or together with D and K and the carbon atoms to which they are attached form a carbocyclic ring or heterocyclic ring having 5 to 8 ring members;

wherein I is hydrogen, hydroxy, halogen, lower alkyl, lower alkoxy, thiol, amino, ester, or an amide comprising —NHCOR$_1$ and wherein is R$_1$ is hydrogen, lower alkyl, or lower alkoxy;

wherein K is alkyl, cycloalkyl, or together with D and G and the carbon atoms to which they are attached form a carbocyclic ring or heterocyclic ring having 5 to 8 ring members; and wherein R is hydrogen or alkyl.

In yet another aspect, the present invention is directed to compounds according to Formula III(A):

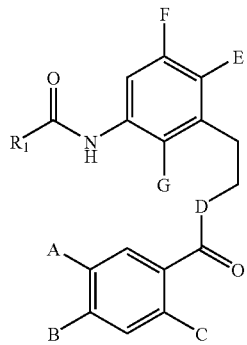

wherein A is hydrogen, chlorine, fluorine, methoxy, ethoxy, phenyl, benzyl, or allyl;

wherein B is hydroxy, chlorine, fluorine, methoxy, ethoxy, or benzoxy;

wherein C is hydroxy, amino, methoxy, or ethoxy;

wherein D is oxygen, alkyl, or —NH—;

wherein E is hydroxy, chlorine, fluorine, methoxy, ethoxy, or —NH$_2$;

wherein F is hydroxy, chlorine, fluorine, thiol, methoxy, ethoxy, amino, or is oxidized to form a ketone;

wherein G is hydroxy, chlorine, fluorine, —NH$_2$, thiol, methoxy, ethoxy, or is oxidized to form ketone; and wherein R$_1$ is hydrogen, lower alkyl, or lower alkoxy.

In yet another aspect, the present invention is directed to compounds according to Formula III(B):

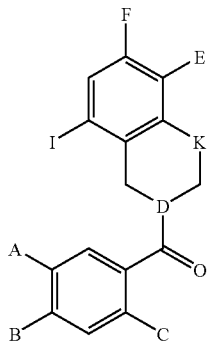

wherein A is hydrogen, chlorine, fluorine, methoxy, ethoxy, phenyl, benzyl, or allyl;

wherein B is hydroxy, chlorine, fluorine, methoxy, ethoxy, or benzoxy;

wherein C is hydroxy, amino, methoxy, or ethoxy;

wherein D is —CH— or amino and together with K and the carbon atoms to which they are attached form a carbocyclic ring or heterocyclic ring having 5 to 8 ring members;

wherein E is hydroxy, chlorine, fluorine, methoxy, ethoxy, or amino;

wherein F is hydroxy, chlorine, fluorine, thiol, methoxy, ethoxy, amino;

wherein I is hydrogen, hydroxy, chlorine, fluorine, methyl, methoxy, ethoxy, or —NH$_2$; and wherein K is lower alkyl and together with D and the carbon atoms to which they are attached form a carbocyclic ring or heterocyclic ring having 5 to 8 ring members.

In yet another aspect, the present invention is directed to compounds according to Formula III(C):

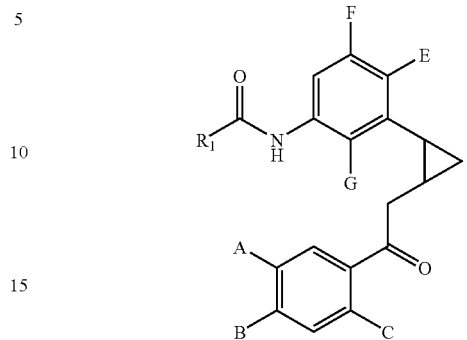

wherein A is hydrogen, chlorine, fluorine, methoxy, ethoxy, phenyl, benzyl, or allyl;

wherein B is hydroxy, chlorine, fluorine, methoxy, ethoxy, or benzoxy;

wherein C is hydroxy, amino, methoxy, or ethoxy;

wherein E is hydroxy, chlorine, fluorine, methoxy, ethoxy, or amino;

wherein F is hydroxy, chlorine, fluorine, thiol, methoxy, ethoxy, amino, or oxidized to form a ketone;

wherein G is hydroxy, chlorine, fluorine, thiol, methoxy, ethoxy, amino, or is oxidized to form a ketone; and wherein is R$_1$ is hydrogen, lower alkyl, or lower alkoxy.

In yet another aspect, the present invention is directed to compounds according to Formula III(D):

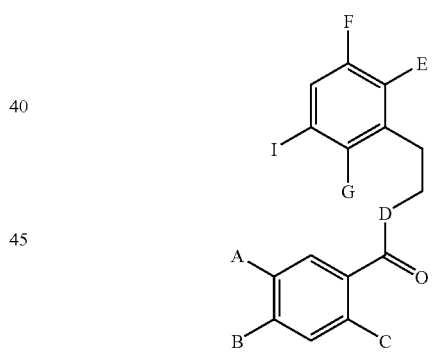

wherein A and B together with the atoms to which they are attached together form a heterocyclic ring having 4 to 10 ring members with at least one heteroatom selected from oxygen, nitrogen, or sulfur;

wherein C is hydroxy, amino, methoxy, or ethoxy;

wherein D is —CH$_2$—, —NH—, oxygen, sulfanyl, sulfenyl, or sulfonyl;

wherein E is chlorine, fluorine, hydroxy, methoxy, ethoxy, or amino;

wherein F is hydroxy, chlorine, fluorine, thiol, methoxy, ethoxy, amino, or is oxidized to from a ketone; and wherein G is hydroxy, chlorine, fluorine, amino, thiol, methoxy, ethoxy, or is oxidized to form a ketone; and wherein I is hydrogen, hydroxy, chlorine, fluorine, methyl, methoxy, ethoxy, or amino.

In yet another aspect, the present invention is directed to compounds according to Formula III(E):

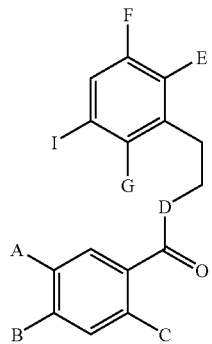

wherein A is hydrogen, chlorine, fluorine, methoxy, ethoxy, phenyl, benzyl, or allyl;

wherein B is hydroxy, chlorine, fluorine, methoxy, ethoxy, or benzoxy;

wherein C is hydroxy, amino, methoxy, or ethoxy;

wherein D is —$CH_2$—, —NH—, oxygen, sulfanyl, sulfenyl, or sulfonyl;

wherein E and F together with the atoms to which they are attached together form a heterocyclic ring having 4 to 10 ring members with at least one heteroatom selected from oxygen, nitrogen, or sulfur;

wherein G is hydroxy, chlorine, fluorine, amino, thiol, methoxy, ethoxy, or oxidized to form a ketone; and wherein I is hydrogen, hydroxy, chlorine, fluorine, methyl, methoxy, ethoxy, or amino.

In yet another aspect, the present invention is directed to compounds according to Formula III(F):

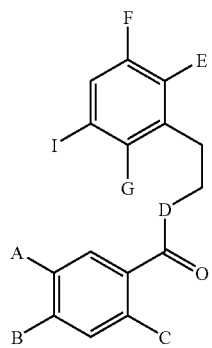

wherein A is hydrogen, chlorine, fluorine, methoxy, ethoxy, phenyl, benzyl, or allyl;

wherein B is hydroxy, chlorine, fluorine, methoxy, ethoxy, or benzoxy;

wherein C is hydroxy, amino, methoxy, or ethoxy;

wherein D is lower alkyl, oxygen, or —NH—;

wherein E is hydroxy, chlorine, fluorine, methoxy, ethoxy, or —$NH_2$;

wherein F is hydroxy, chlorine, fluorine, thiol, methoxy, ethoxy, amino, or is oxidized to form a ketone;

wherein G is hydroxy, chlorine, fluorine, amino, thiol, methoxy, ethoxy, or is oxidized to form a ketone; and wherein I is hydrogen, hydroxy, chlorine, fluorine, methyl, methoxy, ethoxy, or amino.

In another aspect, the present invention is directed to compounds according to Formula III wherein A is halogen; wherein B and C are both hydroxy; wherein D is oxygen; wherein E is lower alkoxy; wherein F and G are both oxidized to form a quinone; wherein I is amino, hydroxy, or halogen; wherein K is alkyl; and wherein R is hydrogen or alkyl.

In still another aspect of the present invention, compounds according to Formula III are provided wherein A is halogen; wherein B and C are both hydroxy; wherein D is oxygen; wherein E is lower alkoxy; wherein F and G are both hydroxy; wherein I is amino, hydroxy, or halogen; wherein K is alkyl; and wherein R is hydrogen or alkyl.

In another aspect, the present invention is directed to compounds of Formula III wherein A is halogen; wherein B and C are both hydroxy; wherein D is oxygen; wherein E, F, and G are all lower alkoxy; wherein I is amino, hydroxy, or halogen; wherein K is alkyl; and wherein R is hydrogen or alkyl.

In yet another aspect, compounds of Formula III are provided wherein A is halogen; wherein B and C are both hydroxy; wherein D is oxygen; wherein E is allyl amine; wherein F and G are both oxidized to form a quinone; wherein I is amino, hydroxy, or halogen, wherein K is alkyl; and wherein R is hydrogen or alkyl.

In still another aspect, compounds according to Formula III are provided wherein A is phenyl; wherein B and C are both hydroxy; wherein D is oxygen; wherein E, F, and G are all lower alkoxy; wherein I is amino, hydroxy, or halogen; wherein K is alkyl; and wherein R is hydrogen or alkyl.

In yet another aspect, the present invention is directed to compounds according to Formula III wherein A is halogen; wherein B is lower alkoxy; wherein C is hydroxy; wherein D is oxygen; wherein E, F, and G are all lower alkoxy; wherein I is amino, hydroxy, or halogen; wherein K is alkyl; and wherein R is hydrogen or alkyl.

In a further aspect, the present invention is directed to compounds according to Formula III wherein A is halogen; wherein B and C are both hydroxy; wherein D is oxygen; wherein E, F, and G are all lower alkoxy; wherein I is amino, halogen, or hydroxy; wherein K is alkyl; and wherein R is hydrogen or alkyl.

In still another aspect, the present invention is directed to compounds according to Formula III wherein A is halogen; wherein B and C are both hydroxy; wherein D is oxygen; wherein E, F, and G are all lower alkoxy; wherein I is amino, halogen, or hydroxy; wherein K is lower alkyl; and wherein R is hydrogen or alkyl.

In yet another aspect, the present invention is directed to compounds of Formula III wherein both G and F are oxidized to form a quinone.

In yet another aspect, the present invention is directed to compounds of Formula III wherein B and C are both hydroxy.

In yet another aspect, the present invention is directed to compounds of Formula III wherein A is halogen.

In yet another aspect, the present invention is directed to compounds of Formula III wherein R is hydrogen.

In yet another aspect, the present invention is directed to compounds of Formula III wherein G and F are both hydroxy.

In yet another aspect, the present invention is directed to compounds of Formula III wherein E, F, and G are each lower alkoxy.

In yet another aspect, the present invention is directed to compounds of Formula III wherein F and G are oxidized to form a quinone, and E is allyl amine.

In yet another aspect, the present invention is directed to compounds according to Formula IV:

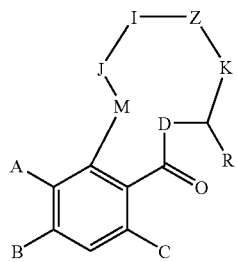

wherein A is hydrogen, halogen, lower alkyl, lower alkoxy, aryl, aralyl, allyl, or together with B and the atoms to which they are attached form a heterocyclic ring having 4 to 12 ring members with at least one heteroatom selected from oxygen, nitrogen, or sulfur;

wherein B is hydroxy, amino, halogen, lower alkoxy, aralkoxy, or together with A and the atoms to which they are attached form a heterocyclic ring having 4 to 12 ring members with at least one heteroatom selected from oxygen, nitrogen, or sulfur;

wherein C is hydroxy, amino, lower alkoxy;

wherein D is alkyl, oxygen, or amino, sulfanyl, sulfenyl, or sulfonyl;

wherein I is alkyl, amino, carbonyl, sulfanyl, sulfenyl, sulfonyl, or oxygen;

wherein J is alkyl, amino, carbonyl, sulfanyl, sulfenyl, sulfonyl, or oxygen;

wherein M is alkyl or cycloalkyl;

wherein K is alkyl or cycloalkyl;

wherein R is hydrogen or alkyl; and wherein Z is either one of the following heterocycles

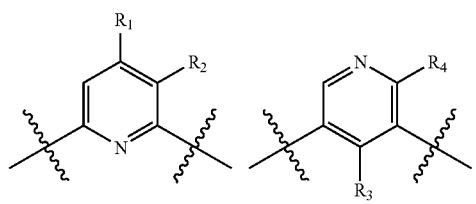

wherein $R_1$ is hydroxy, halogen, thiol, lower alkoxy, amino, or oxidized to form a ketone;

wherein $R_2$ is hydroxy, halogen, lower alkoxy, amino, or allyl amine;

wherein $R_3$ is hydrogen, halogen, lower alkyl, lower alkoxy, or oxidized to form a ketone; and wherein $R_4$ is hydroxy, halogen, lower alkoxy, amino, or allyl amine.

In yet another aspect, the present invention is directed to compounds according to Formula IV wherein Z is selected from one of the following heterocycles

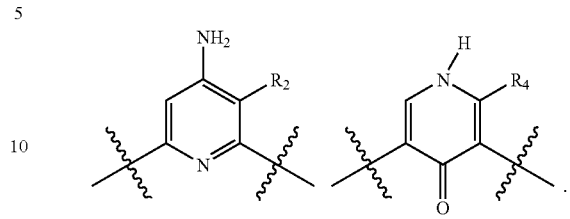

In yet another aspect, the present invention is directed to compounds according to Formula V:

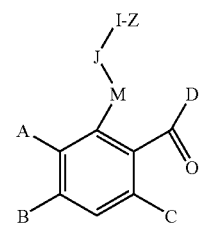

wherein A is hydrogen, halogen, lower alkyl, lower alkoxy, aryl, aralyl, allyl, or together with B and the atoms to which they are attached form a heterocyclic ring having 4 to 12 ring members with at least one heteroatom selected from oxygen, nitrogen, or sulfur;

wherein B is hydroxy, amino, halogen, lower alkoxy, aralkoxy, or together with A and the atoms to which they are attached form a heterocyclic ring having 4 to 12 ring members with at least one heteroatom selected from oxygen, nitrogen, or sulfur;

wherein C is hydroxy, amino, or lower alkoxy;

wherein D is hydroxy, lower alkyl, lower alkoxy, amino, or together with M and the carbon atoms to which they are attached and the carbon at position 2 form a carbocyclic ring having 5 to 8 ring members;

wherein I is alkyl, amino, carbonyl, sulfanyl, sulfenyl, sulfonyl, or oxygen;

wherein J is alkyl amino, carbonyl, sulfanyl, sulfenyl, sulfonyl, or oxygen; and wherein M is alkyl, cycloalkyl; or M together with D and the carbon atoms to which they are attached form a heterocylic ring having 4 to 12 ring members with at least one heteroatom selected from oxygen, nitrogen, and sulfur; or M is alkyl and together with D and the carbon atoms to which they are attached form a heterocylic ring having 4 to 12 ring members with at least one heteroatom selected from oxygen, nitrogen, and sulfur.

wherein Z is selected from one of the following heterocycles

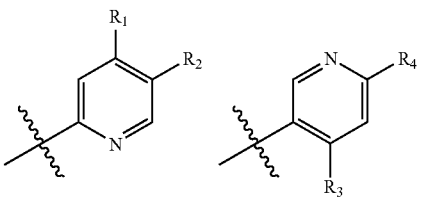

wherein $R_1$ is hydroxy, halogen, thiol, lower alkoxy, amino, or oxidized for form a ketone;

wherein $R_2$ is hydroxy, halogen, lower alkoxy, amino, or allyl amine;

wherein $R_3$ is hydrogen, halogen, lower alkyl, lower alkoxy, or oxidized to form a ketone; and wherein $R_4$ is hydroxy, halogen, lower alkoxy, amino, or allyl amine.

In yet another aspect, the present invention is directed to compounds according to Formula V wherein Z is selected from one of the following heterocycles

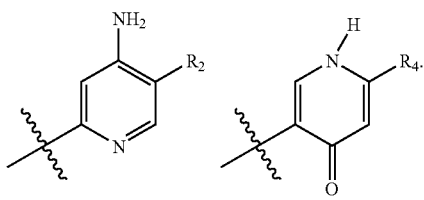

In yet a further aspect, the present invention is directed to compounds according to Formula VI:

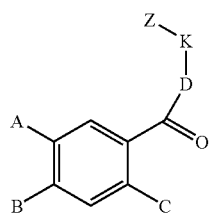

wherein A is hydrogen, halogen, lower alkyl, lower alkoxy, aryl, aralyl, allyl, or together with B and the atoms to which they are attached form a heterocyclic ring having 4 to 12 ring members with at least one heteroatom selected from oxygen, nitrogen, or sulfur;

wherein B is hydroxy, amino, halogen, lower alkoxy, aralkoxy, or together with A and the atoms to which they are attached form a heterocyclic ring having 4 to 12 ring members with at least one heteroatom selected from oxygen, nitrogen, or sulfur;

wherein C is hydroxy, amino, lower alkoxy;

wherein D is alkyl, oxygen, amino, sulfanyl, sulfenyl, or sulfonyl;

wherein K is alkyl or cycloalkyl; and wherein Z is selected from one of the following heterocycles

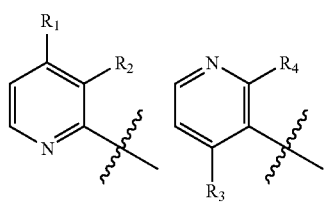

wherein $R_1$ is hydroxy, halogen, thiol, lower alkoxy, amino, or oxidized to form a ketone;

wherein $R_2$ is hydroxy, halogen, lower alkoxy, amino, or allyl amine;

wherein $R_3$ is hydrogen, halogen, lower alkyl, lower alkoxy, or oxidized to form a ketone; and wherein $R_4$ is hydroxy, halogen, lower alkoxy, amino, or allyl amine.

In yet another aspect, the present invention is directed to compounds according to Formula VI wherein Z is selected from one of the following heterocycles

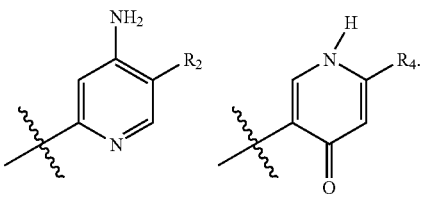

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
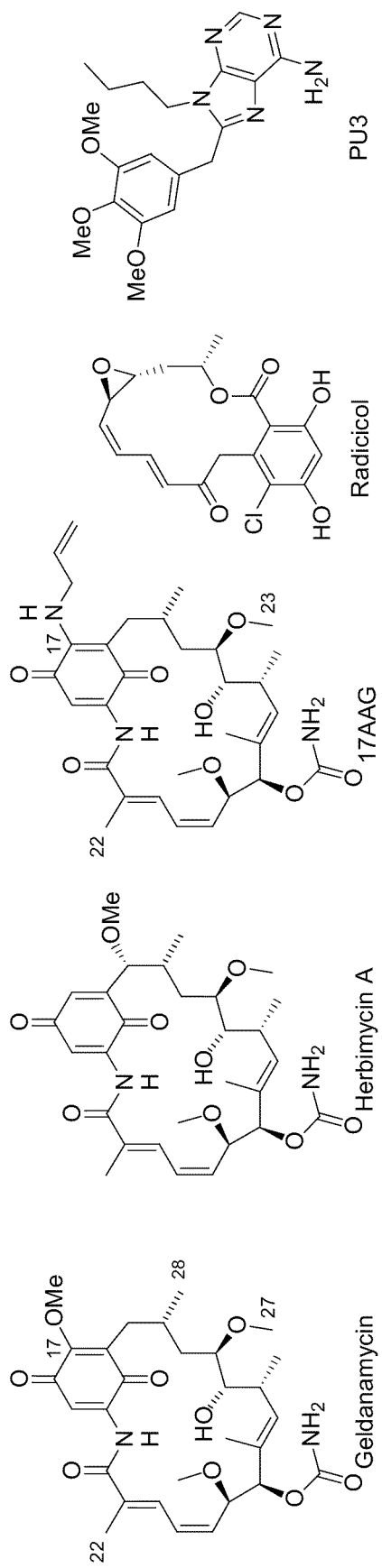
FIG. 1 illustrates the structure of several prior art Hsp90 inhibitors.
Figure 2:
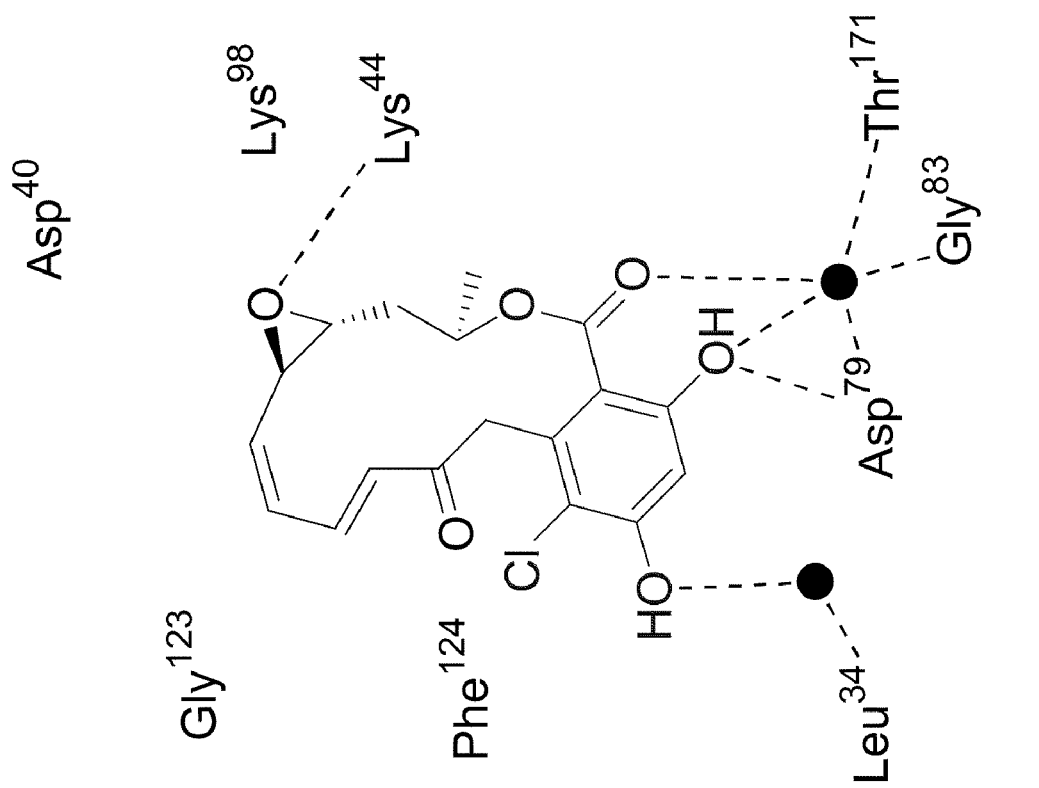
FIG. 2 illustrates the binding of GDA and RDC to Hsp90.
Figure 2:
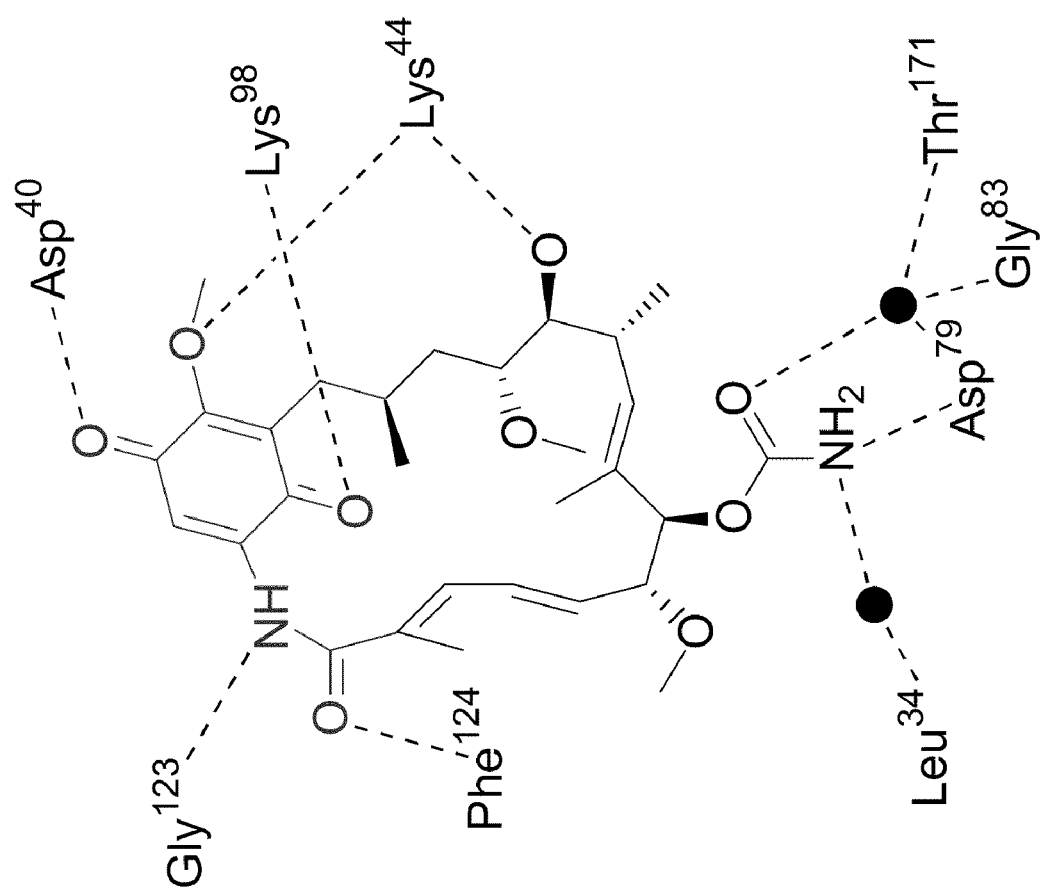

Molecular terms, when used in this application, have their common meaning unless otherwise specified. It should be noted that the alphabetical letters used in the formulas of the present invention should be interpreted as the functional groups, moieties, or substitutents as defined herein. That is, those skilled in the art will readily understand that B, C, F, I, K, etc. do not refer to boron, carbon, fluorine, iodine, potassium etc. but are instead defined as set forth herein. Unless otherwise defined, the symbols will have their ordinary and customary meaning to those skilled in the art.

The term "amino" signifies a primary, secondary or tertiary amino group bonded via the nitrogen atom, with the secondary amino group carrying an alkyl, cycloalkyl, or other amino (in the case of a hydrazide) substituent and the tertiary amino group carrying two similar or different alkyl, cycloalkyl, or other amino (in the case of a hydrazide) substituents or the two nitrogen substituents together forming a ring, such as, for example, —$NH_2$, methylamino, ethylamino, dimethylamino, diethylamino, methyl-ethylamino, pyrrolidin-1-yl or piperidino, etc.

The term "alkyl" refers to an optionally substituted branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred "alkyl" groups herein contain 1 to 12 carbon atoms. "Lower alkyl" refers to an alkyl group of one to six, more preferably one to four, carbon atoms.

The term "alkoxy" denotes oxy-containing groups substituted with an alkyl, cycloalkyl, or heterocyclyl group. Examples include, without limitation, methoxy, ethoxy, tert-butoxy, benzyloxy, and cyclohexyloxy. Most preferred are "lower alkoxy" groups having one to six carbon atoms. Examples of such groups include methoxy, ethoxy, propoxy, butoxy, isopropoxy, and tert-butoxy alkyls.

The term "aryl" means an optionally substituted carbocyclic aromatic system containing one, two or three rings wherein such rings may be attached together in a pendant manner or may be fused. The term "fused" means that a second ring is present (i.e., attached or formed) by having two adjacent atoms in common (i.e., shared) with the first ring. The term "fused" is equivalent to the term "condensed." The term "aryl" embraces aromatic groups such as phenyl, naphthyl, tetrahydronaphthyl, indane, and biphenyl.

The term "aralkyl" embraces aryl-substituted alkyl moieties. Preferable aralkyl groups are "lower aralkyl" groups having aryl groups attached to alkyl groups having one to six carbon atoms. Examples of such groups include benzyl, diphenylmethyl, triphenylmethyl, phenylethyl, and diphenylethyl. The terms benzyl and phenylmethyl are interchangeable.

The term "aryloxy" embraces aryl groups, as defined above, attached to an oxygen atom. Examples of such groups include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 4-tert-butylphenoxy, 3-pentafluoroethylphenoxy, and 3-(1,1,2,2-tetrafluoroethoxy)phenoxy.

The term "aralkoxy" embraces oxy-containing aralkyl groups attached through an oxygen atom to other groups. More preferred aralkoxy groups are "lower aralkoxy" groups having phenyl groups attached to lower alkoxy group as described above. Examples of such groups include benzyloxy, 1-phenylethoxy, 3-trifluoromethoxybenzyloxy, 3-trifluoromethylbenzyloxy, 3,5-difluorobenzyloxy, 3-bromobenzyloxy, 4-propylbenzyloxy, 2-fluoro-3-trifluoromethylbenzyloxy, and 2-phenylethoxy.

The term "carbonyl" denotes a carbon group having two of the four covalent bonds shared with an oxygen atom. The term "carboxy" embraces a hydroxyl group attached to one of two unshared bonds in a carbonyl group. The term includes, but is not limited to, carboxamide, carboxamidoalkyl, carboxyalkyl, carboalkoxy, and carboaralkoxy groups. The term "carboxamide" embraces amino, monoalkylamino, dialkylamino, monocycloalkylamino, alkylcycloalkylamino, and dicycloalkylamino groups, attached to one of two unshared bonds in a carbonyl group. The term "carboxamidoalkyl" embraces carboxamide groups, as defined above, attached to an alkyl group. The term "carboxyalkyl" embraces a carboxy group, as defined above, attached to an alkyl group. The term "carboalkoxy" embraces alkoxy groups, as defined above, attached to one of two unshared bonds in a carbonyl group.

The term "carboaralkoxy" embraces aralkoxy groups, as defined above, attached to one of two unshared bonds in a carbonyl group.

The term "carbocyclic" refers to an optionally substituted group that contains one or more covalently closed ring structures, and that the atoms forming the backbone of the ring are all carbon atoms. The term thus distinguishes carbocyclic from heterocyclic rings in which the ring backbone contains at least one non-carbon atom.

The terms "cycloalkane" or "cyclic alkane" or "cycloalkyl" refer to a carbocyclic group in which the ring is an optionally substituted cyclic aliphatic hydrocarbon, for example, a cyclic alkyl group preferably with 3 to 12 ring carbons. "Cycloalkyl" includes, by way of example, cyclopropyl, cyclobutyl, cyclopentyl, cyclohexyl, cycloheptyl, or cyclooctyl, and the like.

The terms "halo" or "halogen" refer to fluoro, chloro, bromo or iodo, usually regarding halo substitution for a hydrogen atom in an organic compound. Of the halos, chloro and fluoro are generally preferred with chloro generally being the more preferred.

The term "heterocyclic or heterocycle" means an optionally substituted, saturated or unsaturated, aromatic or non-aromatic cyclic hydrocarbon group with 4 to about 12 carbon atoms, preferably about 5 to about 6, wherein 1 to about 4 carbon atoms are replaced by nitrogen, oxygen or sulfur. The preferred heterocycles are selected from the group consisting of benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperidine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine, and triazole.

The term "oxo" shall refer to the substituent =O.

The term "mercapto" or "thiol" or "sulfhydryl" shall refer to the substituent —SH.

The term "carboxy" shall refer to the substituent —COOH.

The term "sulfanyl" shall refer to the substituent —S—.

The term "sulfenyl" shall refer to the substituent —SO—.

the term "sulfonyl" shall refer to the substituent —SO$_2$—.

"Optional" or "optionally" means that the subsequently described event or circumstance may or may not occur, and that the description includes instances where said event or circumstance occurs and instances in which it does not. "Optionally" is inclusive of embodiments in which the described conditions is present and embodiments in which the described condition is not present. For example, "optionally substituted phenyl" means that the phenyl may or may not be substituted, and that the description includes both unsubstituted phenyl and phenyl wherein there is substitution. "Optionally" is inclusive of embodiments in which the described conditions is present and embodiments in which the described condition is not present.

The compounds of the present invention can exist in tautomeric, geometric or stereoisomeric forms. The present invention contemplates all such compounds, including cis- and trans-geometric isomers, E- and Z-geometric isomers, R— and S— enantiomers, diastereomers, d-isomers, l-isomers, the racemic mixtures thereof and other mixtures thereof, as falling within the scope of the invention.

Also included in the family of compounds of the present invention are the pharmaceutically acceptable salts thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the present invention be prepared from inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of the present invention include metallic salts made from aluminum, calcium, lithium, magnesium, potassium, sodium and zinc or organic salts made from N,N'-dibenzylethyleneldiamine, choline, chloroprocaine, diethanolamine, ethylenediamine, meglumine (N-methylglucamine) and procain. All of these salts may be prepared by conventional means from the corresponding compounds of by reacting, for example, the appropriate acid or base with the compounds of the present invention.

The "patient" to be treated with the compounds of the present invention can be any animal, and is preferably a mammal, such as a domesticated animal or a livestock animal. More preferably, the patient is a human.

A "therapeutically effective amount" is an amount of a compound of the present invention or a combination of two or more such compounds, which inhibits, totally or partially, the progression of the condition or alleviates, at least partially, one or more symptoms of the condition. A therapeutically effective amount can also be an amount that is prophylactically effective. The amount that is therapeutically effective will depend upon the patient's size and gender, the condition to be treated, the severity of the condition and the result sought. For a given patient, a therapeutically effective amount can be determined by methods known to those of skill in the art. In reference to the treatment of cancer using the compounds of the present invention, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

Several of the compounds of the present invention have been shown to inhibit Hsp90 in vitro. As such, it is contemplated that therapeutically effective amounts of the compounds of the present invention will be useful as anti-cancer agents.

The following examples are provided to illustrate the present invention and are not intended to limit the scope thereof. Those skilled in the art will readily understand that known variations of the conditions and processes of the following preparative procedures can be used to prepare these compounds.

EXAMPLE 1

Synthesis of RAD

This example is directed to the formation of RAD, a chimeric compound having both the quinone moiety of GDA and the 2,4-diphenol moiety of RDC.

Step 1: Preparation of Alcohol to Generate Quinone Moiety

The first step in the synthesis of RAD involves preparation of alcohol precursors containing a quinone moiety that will mimic the quinone moiety of GDA. To prepare these precursors, trimethoxy benzene underwent ortho-lithiation with N-butyl lithium to generate the lithium anion (Gilman et al. 1944) followed by addition of either propylene oxide or ethylene oxide to provide the secondary or primary two-carbon derivatives as shown in scheme below. Nitration of these electron-rich aromatic rings gave the desired regioisomeric nitrated ketone and ester products, which were subsequently reduced to furnish the corresponding secondary and primary alcohols, 1A and 1B, in excellent yields. As shown below, 3-nitro-2,5,6-trimethoxy benzaldehyde (Andrus 2001) was reduced with sodium borohydride to provide the one-carbon alcohol linker, 1C. To prepare the 3-carbon derivative, the aldehyde was homologated to the corresponding α,β-unsaturated methyl ester and reduced to furnish the saturated compound. Nitration and hydrolysis of the resultant acetate (via AcOH/H$^+$) furnished the propyl-derived alcoholic product, 1D.

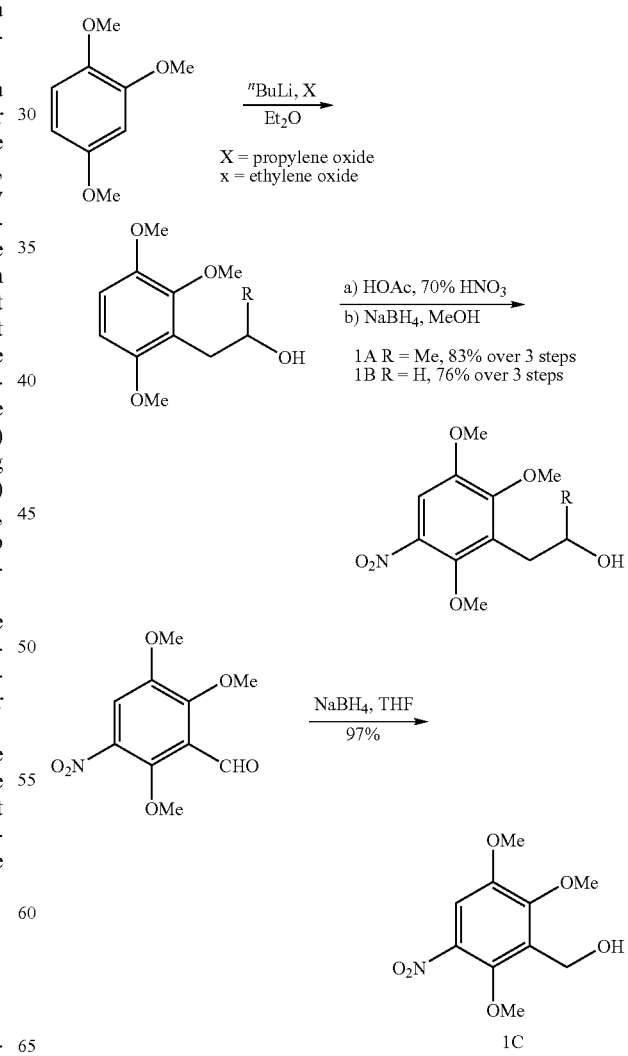

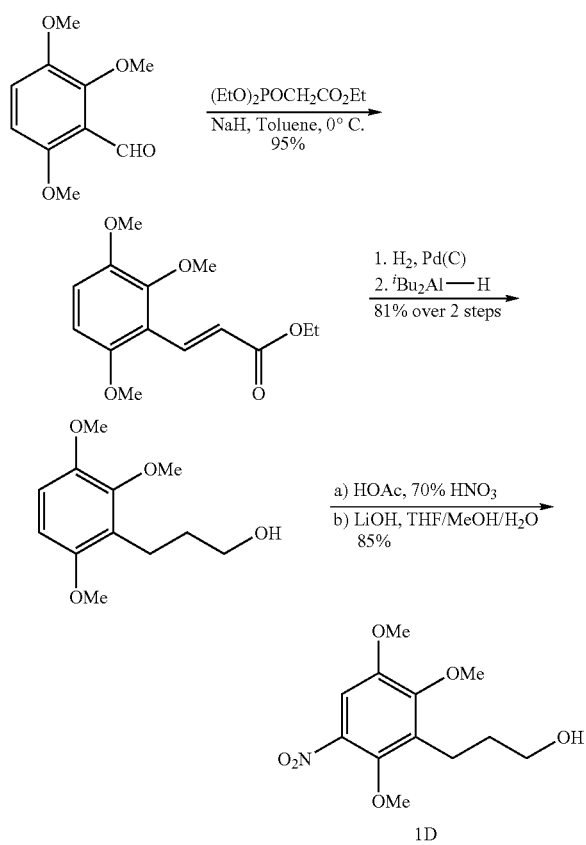

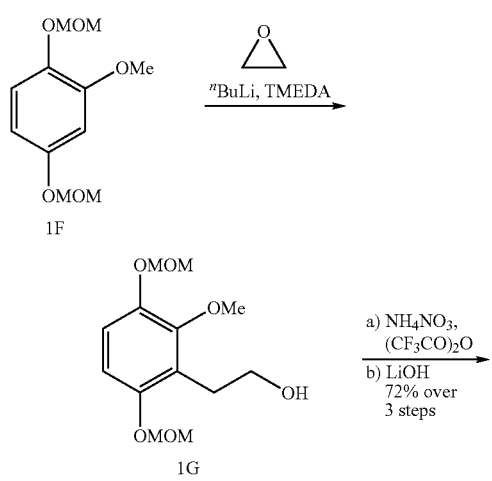

In addition, a bis(MOM) protected quinone precursor compound 1H can be prepared using a similar approach. More specifically, 2-methoxy-1,4-bis(methoxymethyleneoxy)benzene 1F was treated with N-butyl lithium in the presence of N,N,N',N'-tetramethylethylenediamine to provide the lithium anion, which was treated with ethylene oxide to provide 1G. The aromatic ring was subjected to nitration conditions according to the procedure of Crivello (1998) to provide the trifluoroacetate derived product, which was removed by the addition of lithium hydroxide to furnish 1H.

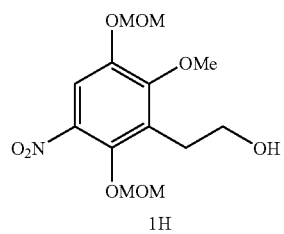

A similar strategy can be employed to provide a MOM-protected secondary alcohol, propyl-derived alcohol, and one carbon alcohol similar to 1B, 1C, and 1D discussed above.

Step 2: Preparation of Alcohol Containing 2,4-Dihydroxyphenol Moiety

The second step in the preparation of RAD involves preparing a precursor moiety containing the 2,4-dihydroxyphenol as in RDC. To obtain this precursor, treatment of two equivalents of methyl acetoacetate with sodium hydride followed by addition of N-butyl lithium provides methyl 2,4-dihydroxy-6-methylbenzoate (Furstner 2000) as shown in the scheme below. TBS-protection of the 2,4-diphenol followed by chlorination will give the corresponding bis(silylether) (Carpenter 1984). Addition of lithium diisopropylamide ("LDA") at −78° C. followed by addition of allyl bromide will furnish the allylated product. Quenching the reaction mixture with acid will not only remove the protecting groups, but will also provide an easily separable material. Hydrolysis of the methyl ester with the lithium anion of n-propanethiol (Porwoll 1984) will give the free acid 1I. Selection of these conditions is based on previously reported conditions for similar compounds that provided 2,4-dihydroxybenzoates in excellent yield (Porwoll 1984).

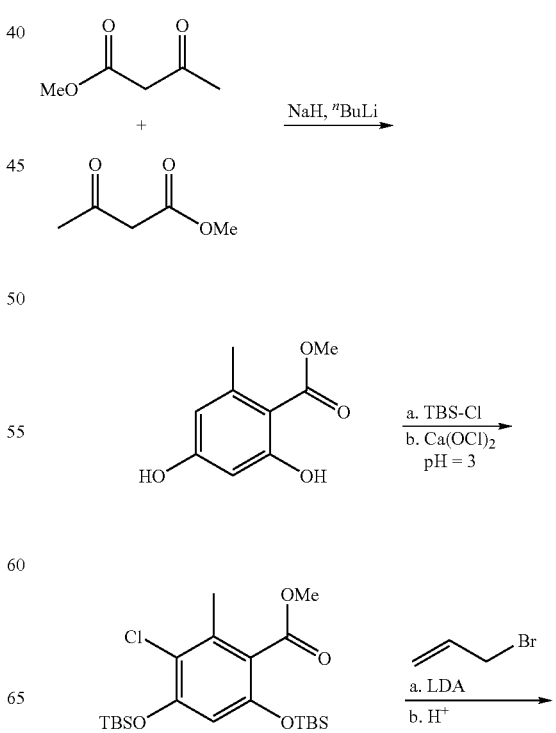

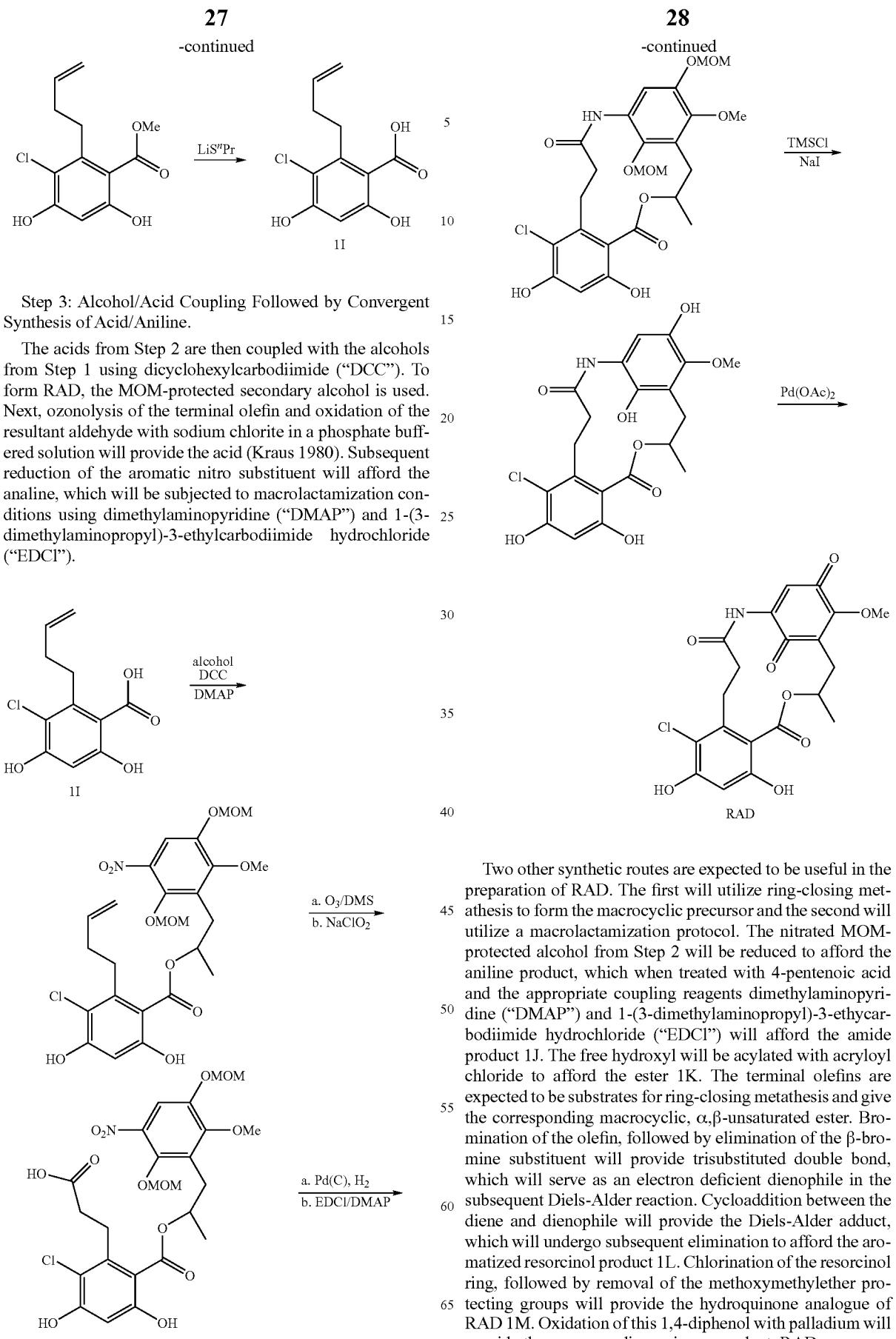

Step 3: Alcohol/Acid Coupling Followed by Convergent Synthesis of Acid/Aniline.

The acids from Step 2 are then coupled with the alcohols from Step 1 using dicyclohexylcarbodiimide ("DCC"). To form RAD, the MOM-protected secondary alcohol is used. Next, ozonolysis of the terminal olefin and oxidation of the resultant aldehyde with sodium chlorite in a phosphate buffered solution will provide the acid (Kraus 1980). Subsequent reduction of the aromatic nitro substituent will afford the analine, which will be subjected to macrolactamization conditions using dimethylaminopyridine ("DMAP") and 1-(3-dimethylaminopropyl)-3-ethylcarbodiimide hydrochloride ("EDCl").

Two other synthetic routes are expected to be useful in the preparation of RAD. The first will utilize ring-closing metathesis to form the macrocyclic precursor and the second will utilize a macrolactamization protocol. The nitrated MOM-protected alcohol from Step 2 will be reduced to afford the aniline product, which when treated with 4-pentenoic acid and the appropriate coupling reagents dimethylaminopyridine ("DMAP") and 1-(3-dimethylaminopropyl)-3-ethycarbodiimide hydrochloride ("EDCl") will afford the amide product 1J. The free hydroxyl will be acylated with acryloyl chloride to afford the ester 1K. The terminal olefins are expected to be substrates for ring-closing metathesis and give the corresponding macrocyclic, α,β-unsaturated ester. Bromination of the olefin, followed by elimination of the β-bromine substituent will provide trisubstituted double bond, which will serve as an electron deficient dienophile in the subsequent Diels-Alder reaction. Cycloaddition between the diene and dienophile will provide the Diels-Alder adduct, which will undergo subsequent elimination to afford the aromatized resorcinol product 1L. Chlorination of the resorcinol ring, followed by removal of the methoxymethylether protecting groups will provide the hydroquinone analogue of RAD 1M. Oxidation of this 1,4-diphenol with palladium will provide the corresponding quinone product, RAD.

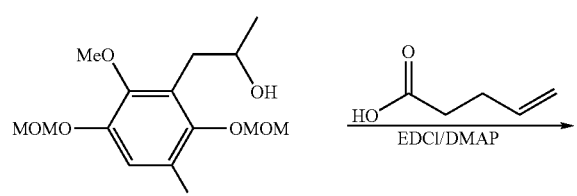

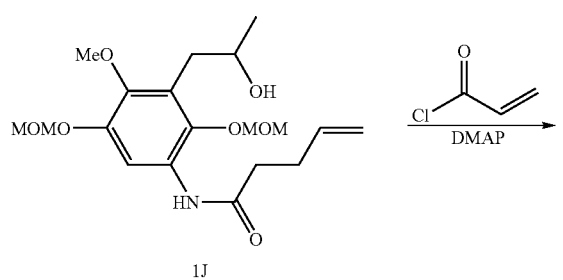

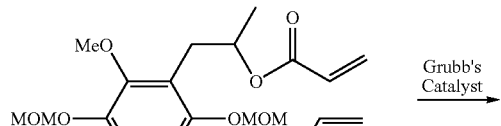

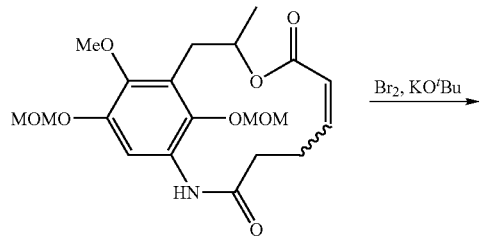

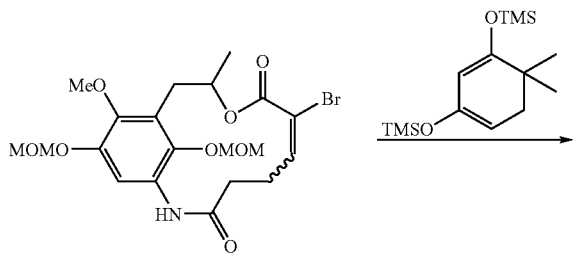

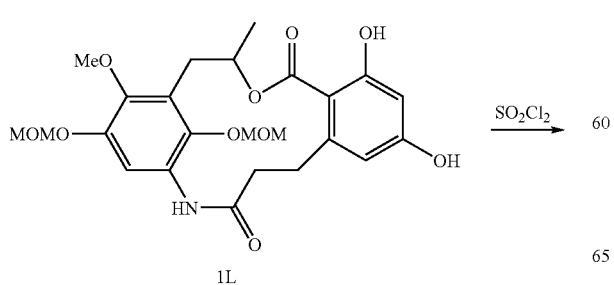

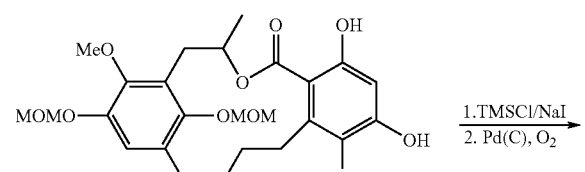

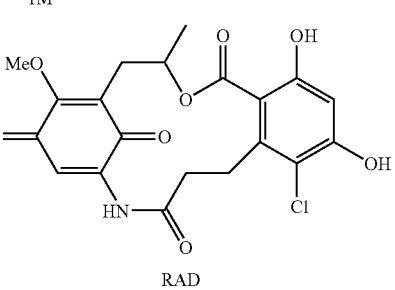

The second alternative route towards the synthesis of RAD begins with olefination of the aldehyde 1N shown below to provide the α,β-unsaturated ethyl ester 10. Bromination of the double bond, followed by treatment with potassium tert-butoxide will provide the trisubstituted olefinic product 1P. Hydrolysis of the ester should afford the acid 1Q, which will be coupled with the free hydroxyl from the aromatic component of the molecule. The dioxolane will be removed under acidic conditions to furnish the aldehyde 1R, that can be subsequently oxidized to the acid 1S. Reduction of the nitro group will provide the amine, which can be coupled to the acid to give the macrocyclic product. The remaining steps to RAD will be accomplished in analogous fashion to the route shown above.

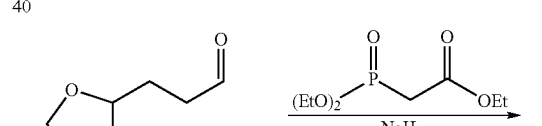

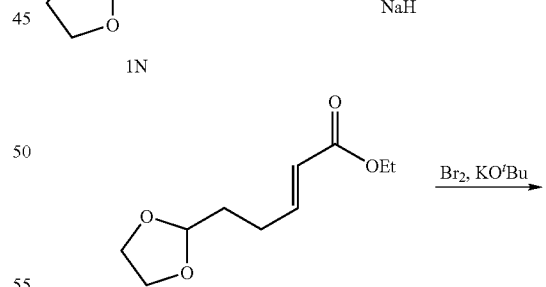

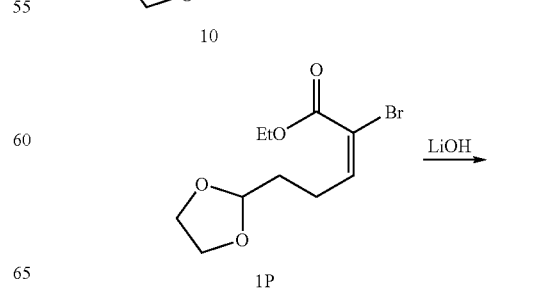

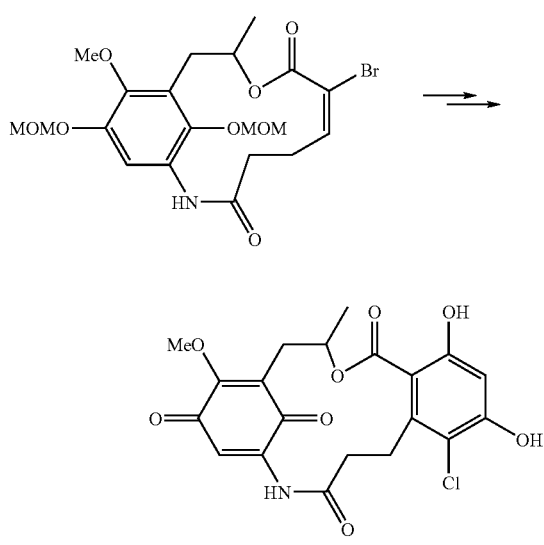

EXAMPLE 2

Synthesis of RAD Derivatives

The synthetic plan proposed for RAD in accordance with the present invention allows assembly of numerous analogs. It is contemplated that structures made in accordance with the present invention may have enhanced selectivity, lower toxicity, and/or greater solubility.

EXAMPLE 2(A)

Modifications to Isopropyl Linker

As discussed above, the C28 methyl substituent of GDA has unfavorable interactions with aspartate 106 in the ATP binding site of bovine Hsp90. See Stebbins et al., *Crystal Structure of Hsp90-Geldanamycin Complex: Targeting of a Protein Chaperone by an Antitumor Agent*, Cell 1997, 89, 239-250, which is incorporated by reference in its entirety. Thus, the present invention includes compounds in which this moiety is removed.

As an example, the desmethyl variant of RAD will be prepared. Alkylation with ethylene oxide in lieu of propylene oxide will be performed as set forth in Step 1 of Example 1. The remaining steps in the synthesis are the same as in Example 1. This produces a compound having a modified ethyl bridge at C18 to C19 in lieu of the isopropyl linker.

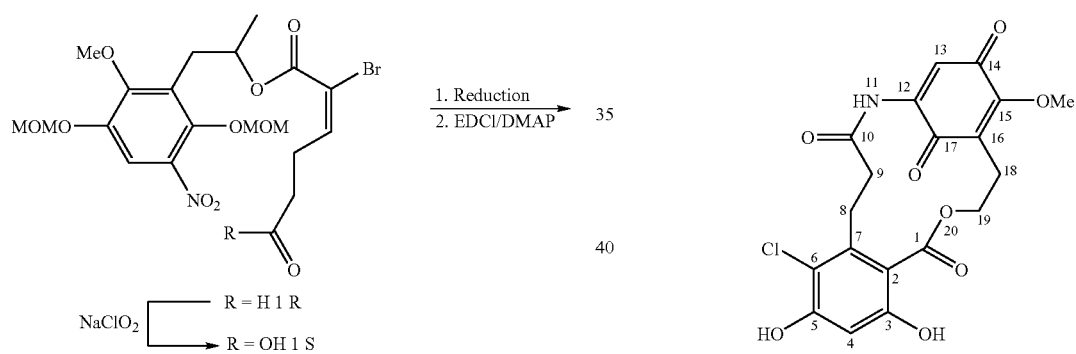

EXAMPLE 2(B)

Modifications to Quinone Ring

The quinone moiety of GDA is redox active, susceptible to nucleophilic addition, and may be responsible for undesired toxicity of GDA unrelated to the inhibition of Hsp90. See Neckers, *Can the Heat Shock Protein 90 Inhibitor Geldanamycin be Designed to Specifically Inhibit HER-2 Tyrosine Kinase?*, Drug Res. Updates. 2000, 3, 203-205, which is incorporated by reference in its entirety. As such, the present invention also includes modifications to the quinone ring of the compounds of the present invention.

The diol will be prepared by modification of the synthetic procedure outlined above. More specifically, 2-methoxy-1,4-dihydroxyhydroquinone will be protected with chloromethyl methyl ether ("MOM-Cl") to provide the bis(MOM)ether and following the previously outlined scheme, will provide a suitable intermediate that can be deprotected after final macrolactamization. The 2-methoxy group of RAD will be displaced with allylamine to furnish the RAD analogue that corresponds to 17-AAG. In addition, the allyl amine can be prepared using well-known techniques.

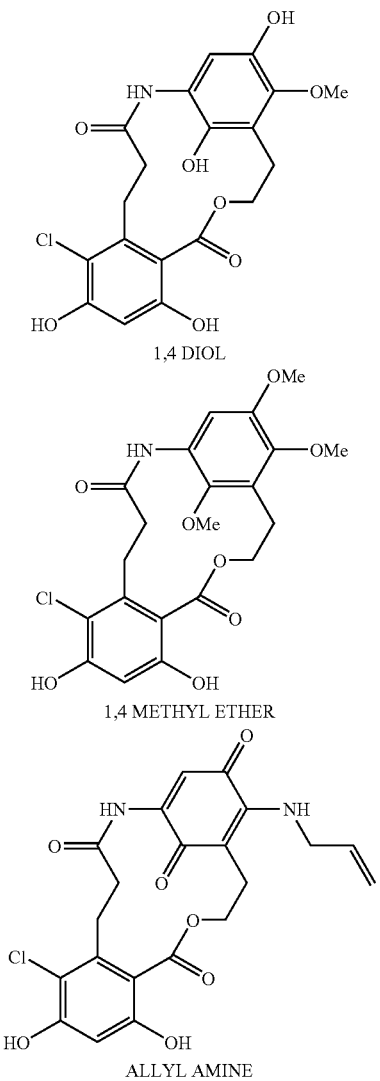

In another aspect of the present invention, in lieu of the quinone, other RAD derivatives in which the C14 is hydroxy, halogen, thiol, lower alkoxy, or amino are within the scope of the present invention. Likewise, RAD derivatives in which the C17 is hydrogen, lower alkyl, or lower alkoxy are within the scope of the present invention.

EXAMPLE 2(C)

Modifications to Chlorine at C6 of Dihydroxyphenyl Moiety

The present invention also includes modifications to the dihydroxyphenol moiety of RAD, and in particular to the chlorine located at the C6 position. The ATP binding site of DNA gyrase is very similar to the N-terminal ATP binding site of Hsp90. Studies have shown that the incorporation of hydrophobic groups into the region corresponding to the chlorine substituent of RDC have resulted in molecules with improved potency. See Boehm et al., *Novel Inhibitors of DNA Gyrase: 3D Structure Based Biased Needle Screening, Hit Validation by Biophysical Methods, and 3D Guided Optimization. A Promising Alternative to Random Screening*. J. Med. Chem. 2000, 43, 2664-2674, which is incorporated by reference in its entirety.

The co-crystal structures of Hsp90 bound to RDC and GDA also show a large hydrophobic cavity containing a hydrophobic group (F124) laying at the bottom of this pocket. See Roe et al., *Structural Basis for Inhibition of the Hsp90 Molecular Chaperone by the Antitumor Antibiotics Radicicol and Geldanamycin*, J. Med. Chem. 1999, 42, 260-266, which is incorporated by reference in its entirety. Thus, the present invention also includes compounds in which the chlorine is modified to incorporate a number of hydrophobic moieties to enhance hydrophobic interactions. Modifications to the C6 position include hydrogen, halogen, lower alkyl, aryl, aralyl, alkoxy, or allyl.

As an example, the RAD-derivative compound of Example 2A is modified to phenyl derivative as shown below. Conversion of the aryl chloride to the phenyl derivative will be accomplished by a palladium mediated cross-coupling reaction. See Li et al., *Highly Active, Air-Stable Palladium Catalysts for the C—C and C—S Bond-Forming Reactions of Vinyl and Aryl Chlorides: Use of Commercially Available [(t-Bu)2P(OH)]2PdCl2, [(t-Bu)2P(OH)PdCl2]2, and [[(t-Bu)2PO...H...OP(t-Bu)2]PdCl]2 as Catalysts*, J. Org. Chem. 2002, 67, 3643-3650, which is incorporated by reference in its entirety.

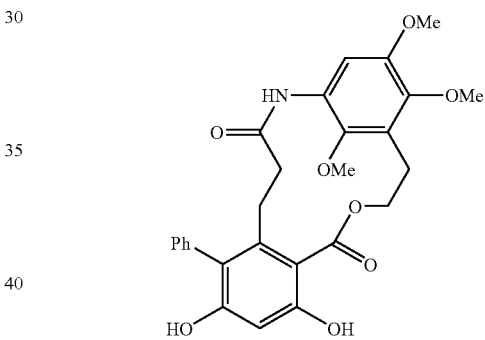

EXAMPLE 2(D)

Modifications to Hydroxyls of Phenol

The present invention also involves derivatives of RAD in which the hydroxyl groups on the 2,4-diphenol are modified with other substituents. Since the 2,4-diphenols of RDC appear to behave consistently with the well-studied hydrogen bond donor/acceptor region of DNA gyrase inhibitors and the co-crystal structure of the N-terminal region of Hsp90 and RDC supports the role of the hydroxyl group ortho to the chlorine substituent as a hydrogen bond acceptor, derivatives that incorporate various alkyl groups in lieu of the hydroxyl will be prepared. Thus, the C5 of RAD may be substituted with hydroxy, amino, halogen, lower alkoxy, or aralkoxy. The C3 of RAD may be substituted with hydroxy, amino, or lower alkoxy.

As an example, the 4-hydroxy of the 2,4-dihydroxybenzoate ring will be selectively alkylated with a variety of small to medium substituents to confirm the hydrogen bond acceptor role of the 4-phenol, while simultaneously providing an opportunity to add lipophobic groups that interact with the adjacent hydrophobic pocket. The 4-hydroxyl can be selectively alkylated in the presence of the 2-hydroxyl because the latter is involved in an intramolecular hydrogen bond with the ester moiety and consequently raises the pKa of 2-hydroxy substituent. See Raphael et al., *P. Synthesis of 2-Indolinones (oxidoles) Related to Mitomycin A*, J. Chem. Soc., Perkin Trans. 1: Org. Bioorg. Chem. 1988, 7, 1823-1828, which is incorporated by reference in its entirety. Thus, the present invention includes compounds having the following structure:

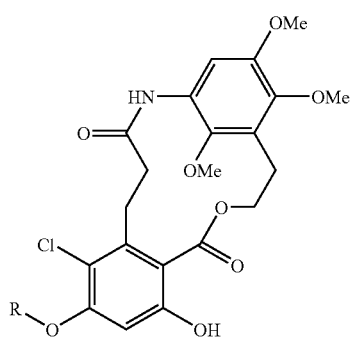

wherein R is lower alkyl.

EXAMPLE 2(E)

N-Substitutions

Because the bound inhibitor rests in a bent conformation, the amide of RAD lies in close proximity to the middle hydrophobic binding region of Hsp90. Consequently, analogues containing N-alkyl substituents, such as those shown below, will also be prepared to increase hydrophobic interactions with Hsp90.

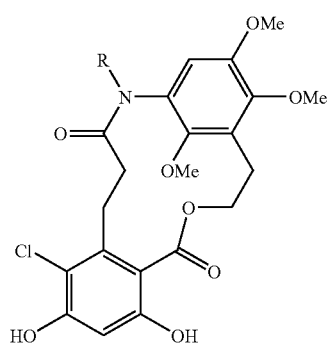

wherein R is lower alkyl.

EXAMPLE 2(F)

Ring Expanders

Ring expanded chimeras incorporating an additional methylene unit in the amide and/or ester side chains will also be synthesized. As an example, those skilled in the art will appreciate that the other alcohols shown in Step 1 of Example 1 can be coupled to the acid to afford different variations of the RAD precursor as shown in the scheme below.

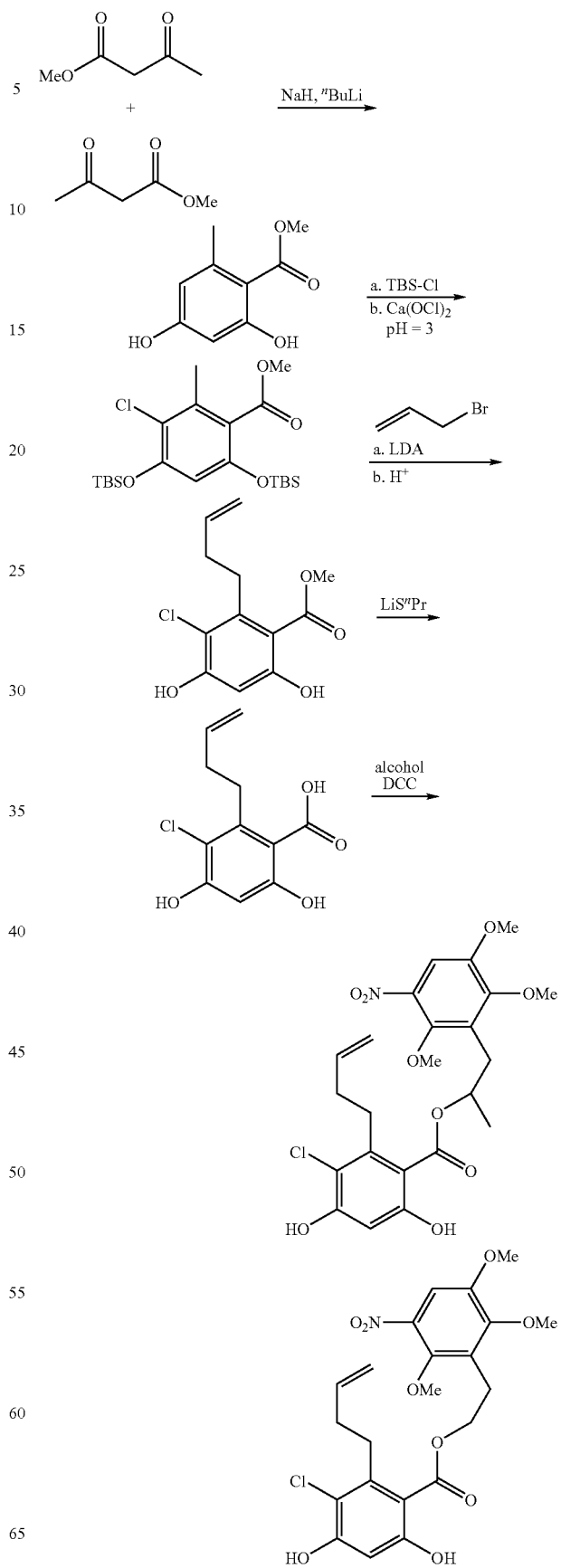

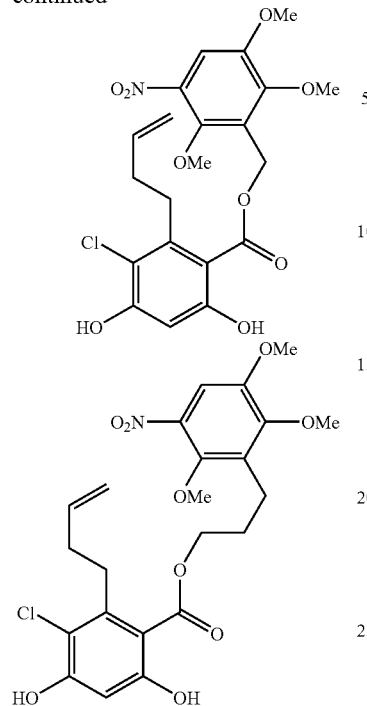

To close the ring, ozonolysis and oxidation with sodium chorite results in the acid. Reduction with palladium results in the analine as set forth in Step 3 of Example 1.

Using the synthesis techniques of this example, those skilled in the art will appreciate how that the present invention is well adapted to prepare compounds of the present invention according to the following formula:

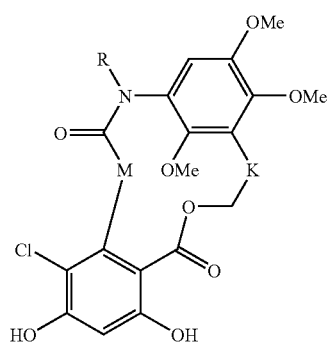

where M is lower alkyl and K is lower alkyl.

EXAMPLE 3

Synthesis of Seco-Ester Derivatives

The present invention also involves the preparation of seco-ester derivatives of RAD.

Step 1: Preparation of Alcohol

To prepare the seco-ester derivatives of the present invention, alcohols were prepared as set forth in Step 1 of Example 1.

Step 2: Preparation of Diphenol Moiety

The 2,4-diphenol portion of seco-ester RAD was prepared by first chlorination (Lampilas 1992) of methyl 2,4-dihydroxybenzoate with sulfonyl chloride, followed by hydrolysis of the methyl ester to give compound 3A in good overall yield.

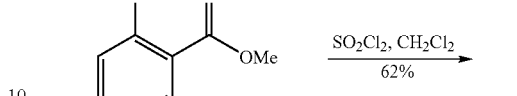

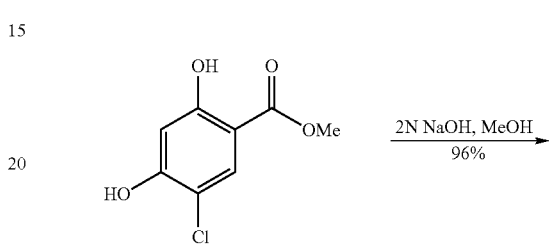

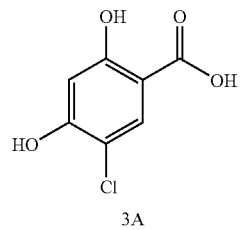

3A

Step 3: Coupling of Alcohols and RAD

After surveying numerous conditions and temperatures it was determined that DCC coupling in the presence of DMAP at 50° C. provided the most reproducible conditions for ester formation as shown in the scheme. Reduction of the nitro substituent to the amine was best when platinum oxide (Yao 1961) was used as a catalyst for hydrogenation. Using the procedure of Yale (1971), the aniline-amines were coupled with phenyl formate to provide the N-formyl aniline products.

The bis-MOM protected compound was prepared via a similar approach as discussed in Example 1, Step 1More specifically, 2-methoxy-1,4-bis(methoxymetheleneoxy)benzene was treated with N-butyl lithium in the presence of N,N,N',N'-tetramethylethylenediamine and then with ethylene oxide. The aromatic ring was then subjected to nitration conditions according to the procedures of Chander and Chapman (1988) to provide the trifluoracetate derived product, which was removed by the addition of lithium hydroxide to furnish the bis(MOM) product in modest yield.

The alcohol 1H was then coupled with 5-chloro-2,4-dihydrozybenzoic acid 3A to produce 3B. The nitro group on 3B was reduced to the amine, which was formulated to give 3D. The bis(methoxymethyleneoxy) protecting groups were removed to provide 3E. Treatment of the hydroquinone with palladium acetate provided the paraquinone product 3F in modest yield.

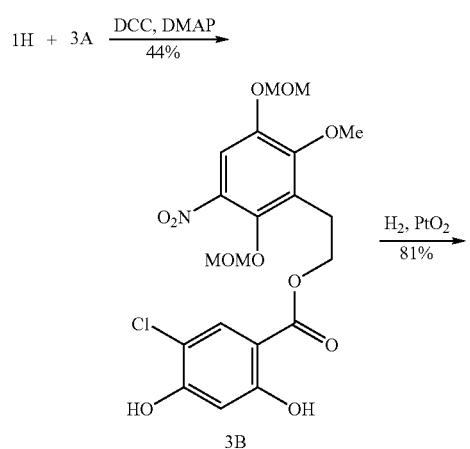

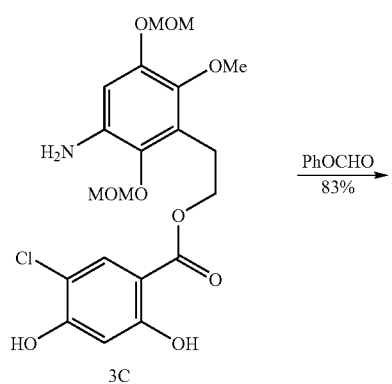

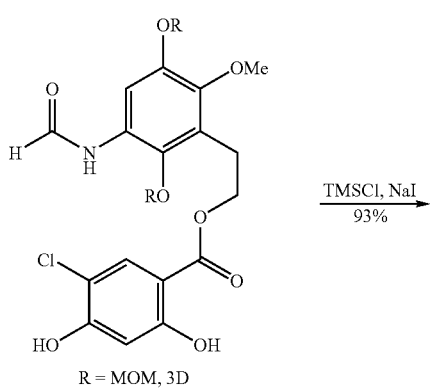

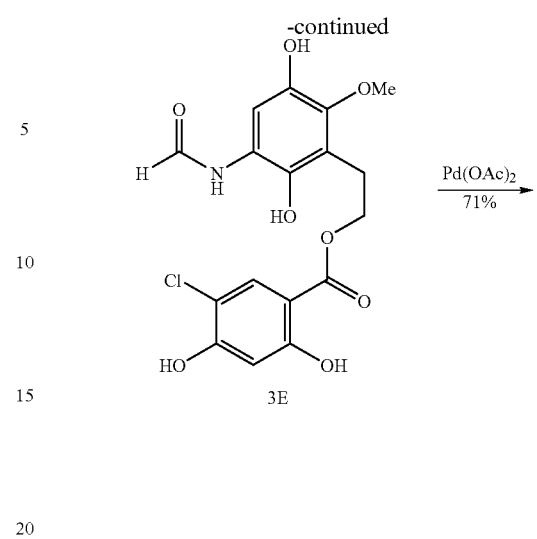

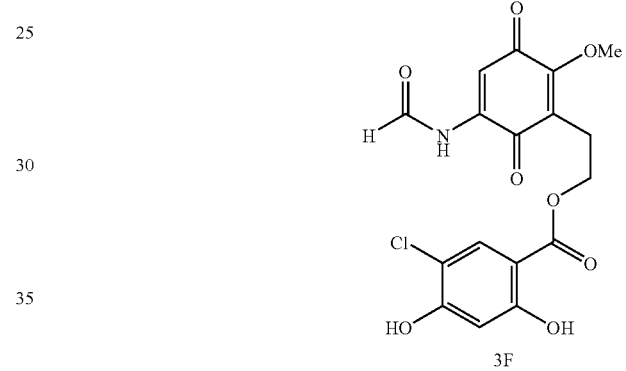

EXAMPLE 4

Synthesis of Seco-Amide RAD

The present invention also involves the preparation of seco-amide derivatives of RAD.

Step 1: Synthesis of Acids containing 1,4-Diphenol-Like Moiety

Acid 4D was be prepared from the same methyl 5-chloro-2,4-di(tert-butyldimethylsilanol)-6-methylbenzoate as previously outlined for the preparation of RAD in Example 1. More specifically, treatment of the benzoate with lithium bis(trimethylsilyl)amide at −78° C. resulted in an anion, (Carpenter 1984) which can be alkylated with either allyl bromide or 4-bromobutene to provide the three-carbon linker, 4B, for seco-amide RAD or the four-carbon homologue. Ozonolysis of the double bond followed by oxidation of the corresponding aldehyde, 4C, provided the intact TBS-containing acids 4D and 4F (Kraus 1980). That is, ozonolysis of the double bond with $O_3$/DMS and oxidation of the resultant aldehyde with $NaClO_2$ gives the acid.

Similarly, the two carbon derivative will be prepared from 4E by treatment with LDA followed by N,N-dimethylformamide to provide the aldehyde, which will be oxidized directly to the corresponding acid, 4G.

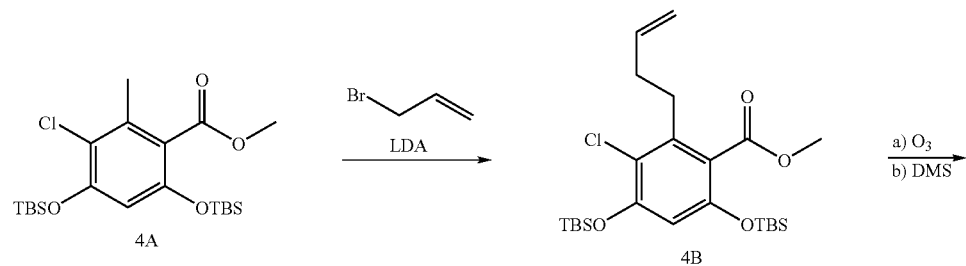
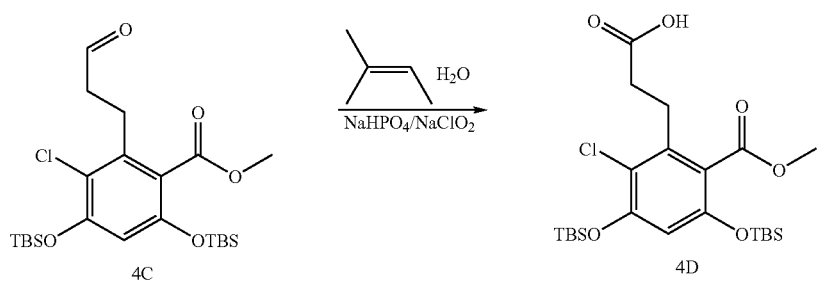
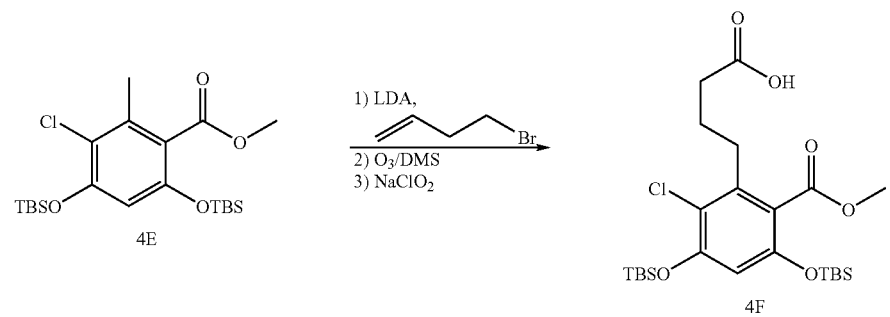
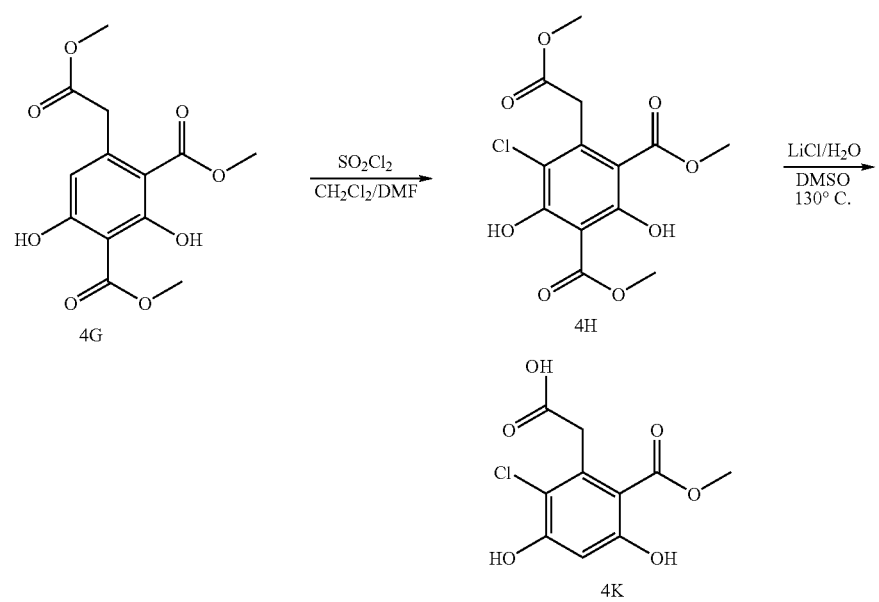

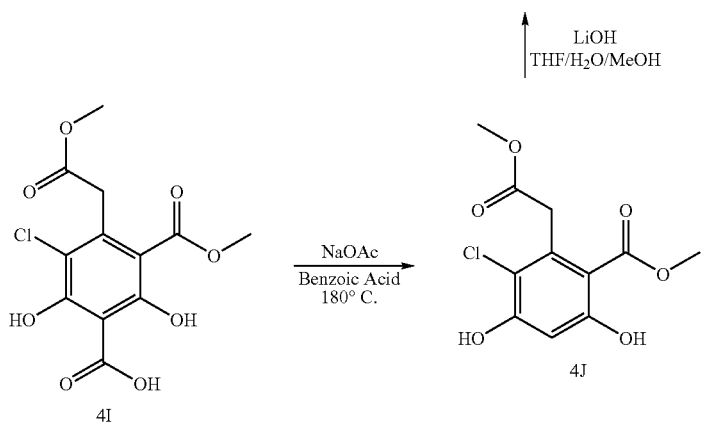

Step 2: Synthesis of Quinone-like Moiety

As discussed above, the quinone precursor was prepared from 1,4-bis(methoxymethoxy)-2-methoxybenzene by nitration (Andrus 2003) and reduction of the nitro group. Since the quinone ring is redox reactive and an excellent Michael acceptor, the preparation of a trimethoxyphenyl derivative was also prepared and is not subject to the same general reactivity as quinones.

Step 3: Coupling the Aniline with Free Carboxylic Acids

The acids from Step 1 where coupled with the analines 4M, 4N to provide corresponding amide products 4O, 4P. Removal of the silyl protecting groups provided 4R and 4S. The methoxymethlether were cleaved in situ with trimethylsilyl iodide to furnish the hydroquinone 4S. See (Andrus 2003). Oxidation with palladium on carbon (Andrus et al., Selective Synthesis of the para-Quinone Region of Geldanamycin, Org. Lett.; (Communication); 2003; 5(21); 3859-3862) gave the paraquinone 4T.

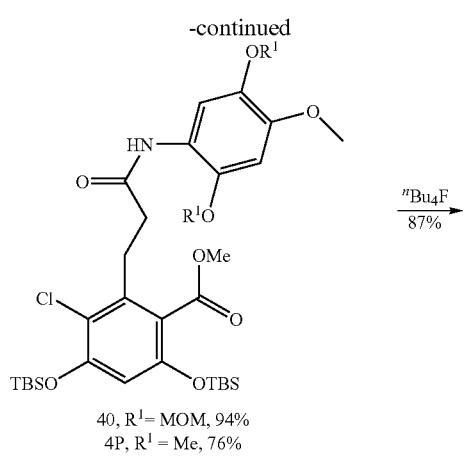

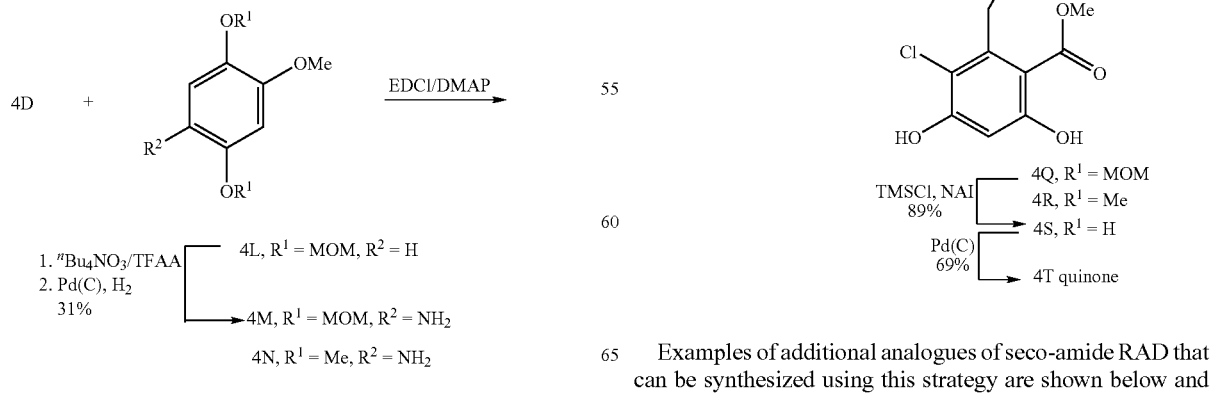

Examples of additional analogues of seco-amide RAD that can be synthesized using this strategy are shown below and complement the proposed analogues of macrocyclic RAD.

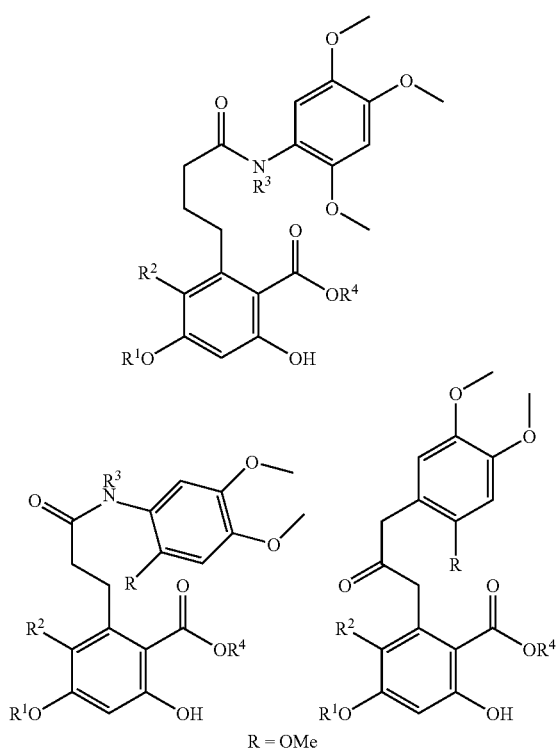

$R^1$ = H, Me, Et, Bn
$R^2$ = Cl, H, Ph, Bn
$R^3$ = H, Me
$R^4$ = Me, Et, Bn

EXAMPLE 5

Modifications to Quinone Ring Core

The present invention is also directed to the use of hydrogen bond acceptors and donors in lieu of the quinone moiety of the compounds of the present invention. As discussed above, the quinone moiety is responsible for undesired cytotoxicity of these natural products and removal of this redox-active and alkylative moiety is anticipated to assist in decreasing the toxicity of the compounds.

Figure 3:
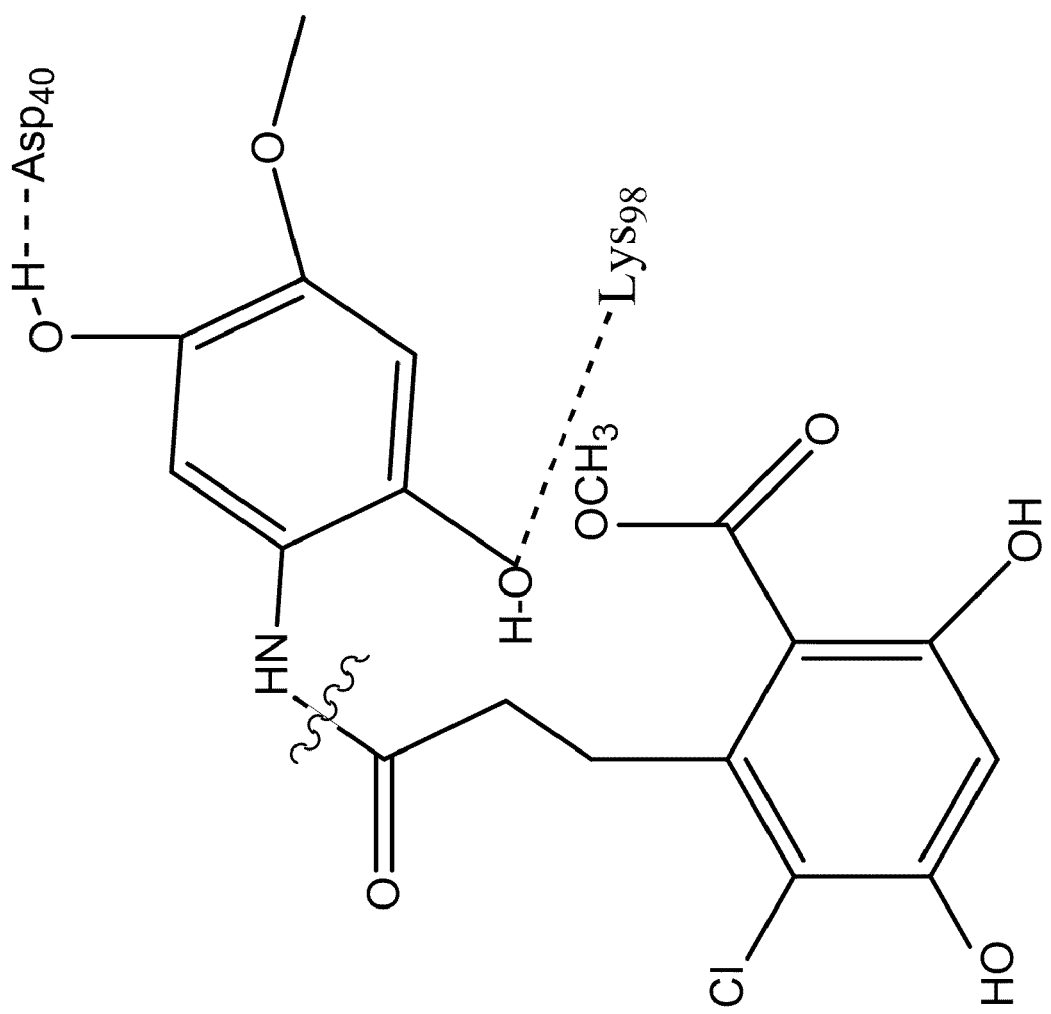
FIG. 3 illustrates the crystal structures of the seco-amide RAD interacting with the Asp40 and Lys98 of Hsp90.

More specifically, it is also contemplated that modified macrocyclic and seco agents of RAD are potent inhibitors of Hsp90. Structure-activity-relationship ("SAR") data on the quinone ring have been produced. The present invention suggests that this functionality acts as a hydrogen bond donor as evidenced by the hydroquinone's greater inhibitory activity (vs. quinone). As shown in FIG. 3, careful reexamination of the co-crystal structure reveals this moiety to interact with Asp4, which is most likely deprotonated at physiological pH. Therefore, the hydrogen bond donor capabilities of the hydroquinone are likely to provide additional interactions with Asp40 when bound to Hsp90, thus resulting in greater inhibitory activity. Since the hydroquinone analogue is capable of acting as both a hydrogen bond donor and acceptor, no detrimental interactions with this amino acid were observed.

In one aspect, the present invention also encompasses the preparation of analogues of the quinone ring which have a moiety that that functions as a hydrogen bond donor and a moiety that functions as hydrogen bond acceptor.

As used herein, the term "hydrogen bond donor" refers to a moiety including a hydrogen atom covalently linked to one electronegatively charged atom (such as oxygen or nitrogen) such that the hydrogen atom becomes electropositively charged and can thus be electrostatically attracted to interact with a second electronegative atom or group of atoms (in either case, the "hydrogen bond acceptor"). Hydrogen bond donor groups are well-known in the art. They include hydroxyl, amines (having at least one hydrogen), a primary or secondary imine group (as part of an amidine or guanidine) or a saturated or unsaturated heterocyclic group containing a ring nitrogen, preferably a group containing 5 to 7 ring atoms. Other, representative hydrogen bond donors include a hydrogen covalently bonded to a nitrogen in an amide bond, and the 2-amino group of guanine.

Hydrogen bond acceptor groups are also well-known in the art. They often include electronegative atoms having lone electron pairs, but also can include aromatic or unsaturated groups having pi electrons available to accept a proton from the hydrogen bond donor. Hydrogen bond acceptor groups include, but are not limited to, hydroxyl, halogen, carbonyl, lower alkoxy, esters, ethers, ketones, carbonates, amines, thiones, thioethers, thiol, sulfones, amides, and sulfide groups.

It is also known that some groups can function as either hydrogen bond donors or hydrogen bond acceptors. These include carboxylic acid groups, urethane or urea groups having at least one hydrogen attached to the nitrogen atom, hydroxyl groups, and amides having at least one hydrogen attached to the nitrogen atom.

All of these "quinone" analogues are readily accessible and will be coupled with the corresponding acid as previously described. For the macrocylic RAD, the quinone ring is preferably modified as follows:

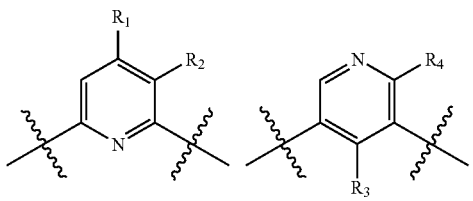

wherein $R_1$ is hydroxy, halogen, thiol, lower alkoxy, amino, or oxidized to form a ketone;

wherein $R_2$ is hydroxy, halogen, lower alkoxy, amino, or allyl amine;

wherein $R_3$ is hydrogen, halogen, lower alkyl, lower alkoxy, or oxidized to form a ketone; and wherein $R_4$ is hydroxy, halogen, lower alkoxy, amino, or allyl amine.

In one aspect, the quinone ring of RAD is modified as follows:

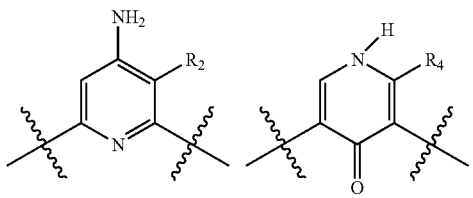

wherein $R_1$, $R_2$, $R_3$, and $R_4$ are defined as above.

Likewise, the corresponding seco-amide derivatives are as follows:

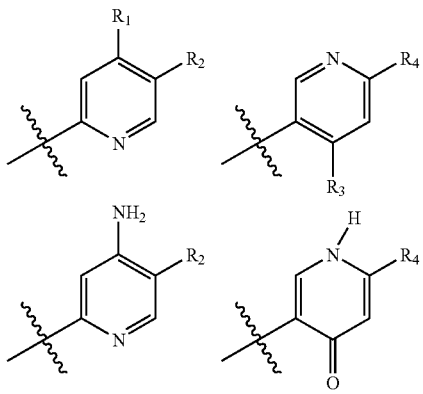

wherein $R_1$, $R_2$, $R_3$, and $R_4$ are defined as above.
Similarly, the seco-ester derivatives are as follows:

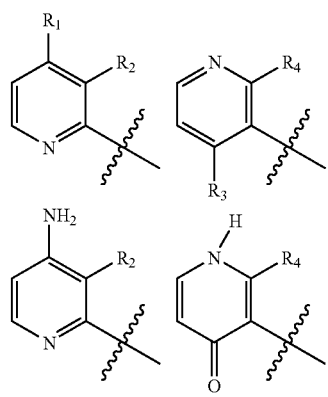

wherein $R_1$, $R_2$, $R_3$, and $R_4$ are defined as above.

The present invention includes compounds that have a high affinity for Hsp90. For example, the molecule 5D shown below contains a cis-amide, but also contains a chiral center to produce a conformationally bent molecule. Benzoxazinones can be prepared by a variety of methods, including acylation and alkylation of ortho-hydroxyanalines with bromo acetylbromide. The resulting benzoxazinone will be treated with base to generate the enolate, which upon addition of an alkyl iodide will furnish the alkylated product shown below. The alkyl iodide will be prepared directly from the corresponding alcohol, which has been previously prepared. The protecting groups will be removed and the molecules separated by chiral HPLC before biological evaluation.

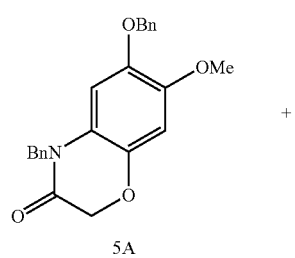

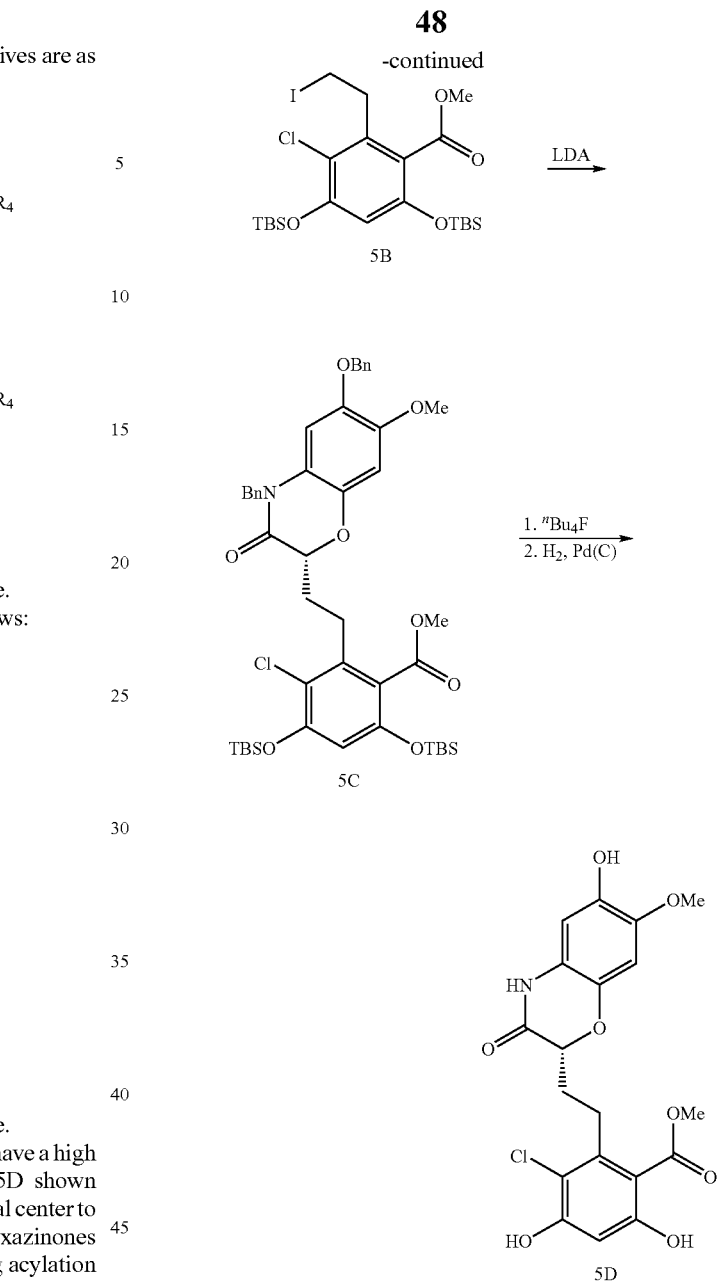

An alternative approach to conformationally biased molecules is to prepare molecules that have a cyclopropane ring in the linker portion of seco-amide RAD. Molecular modeling studies have supported the introduction of a cis-cyclopropane ring into this region and that this portion of the molecule rests in a well defined hydrophobic environment. Cyclopropylradamide 5H will be prepared by Wittig olefination of the aldehyde with bromo(triphenylphosphoranylidene) methyl ester to afford the αβ-unsaturated product as set forth in the scheme below. Treatment of this electron deficient dienophile with an electron rich diene (Barker 2003). should afford the Diels-Alder adduct, which upon work-up (H$^+$) will produce the corresponding aromatic product. Charette's asymmetric cyclopropanation conditions (Charette 1994) will be used to provide the cyclopropylcarbinol product. The primary alcohol will be oxidized to the acid, which will then be coupled with the most desirable quinone analogue to afford the conformationally biased radamide analogues following the procedure outlined herein.

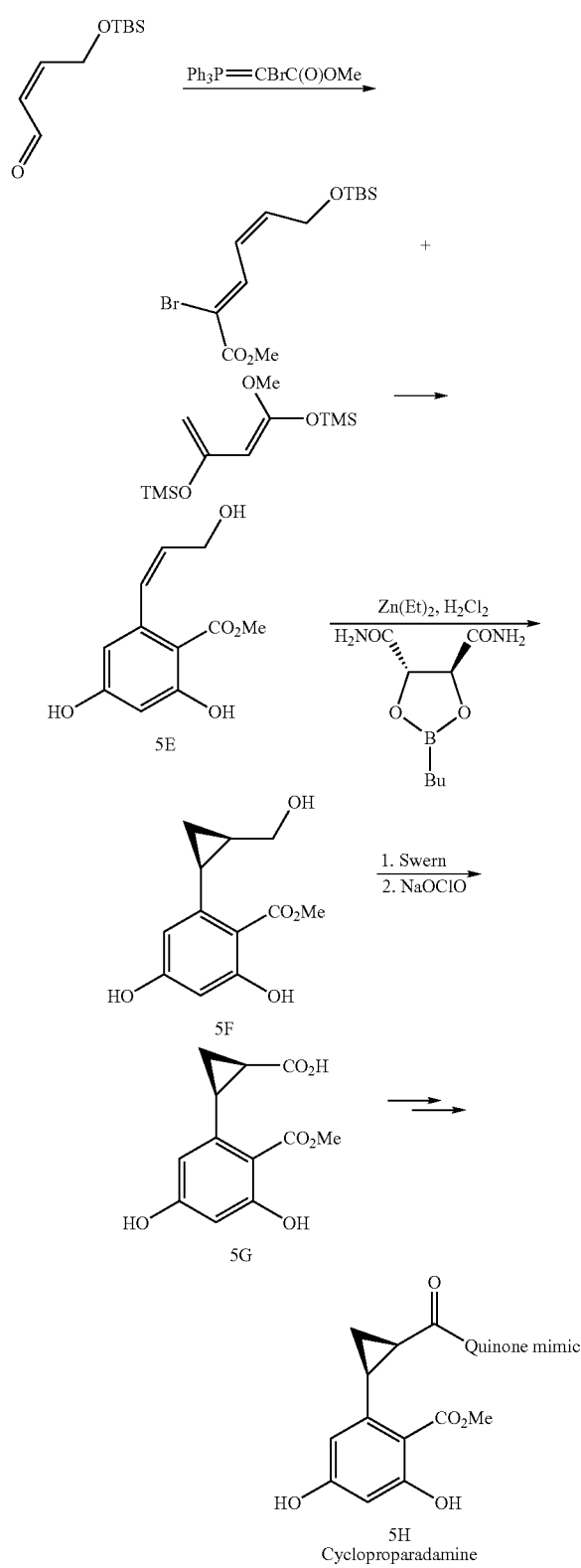

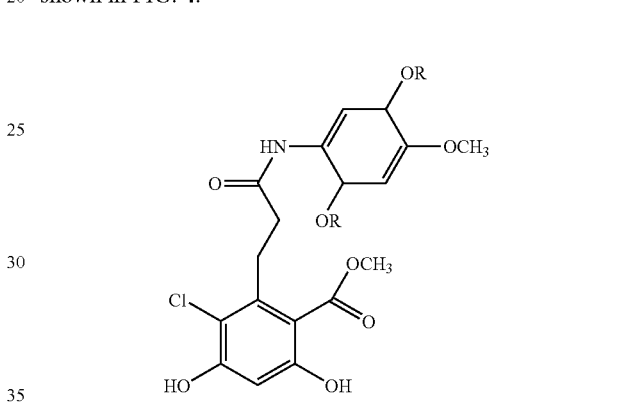

This conformationally biased approach of this example can be used with all of the heterocycles discussed above and includes the linker variants. Similar approaches for the derivatization of seco-ester and macrocyclic RAD are also within the scope of the present invention.

EXAMPLE 6

Biological Activity

The present invention also evaluated the biological activity of some of the RAD amides prepared in accordance with the present invention. Recombinant yeast Hsp90 was overexpressed and purified according to the procedure of Buchner. Richter, et al., *Coordinated ATP Hydrolysis by the Hsp90 Dimer*. J. Biol. Chem. 2001, 276, 33689-33696. The yeast was a kind gift from Boris Kornikaeve at the University of Kansas Biomedical Research Service Laboratory.

Figure 4:
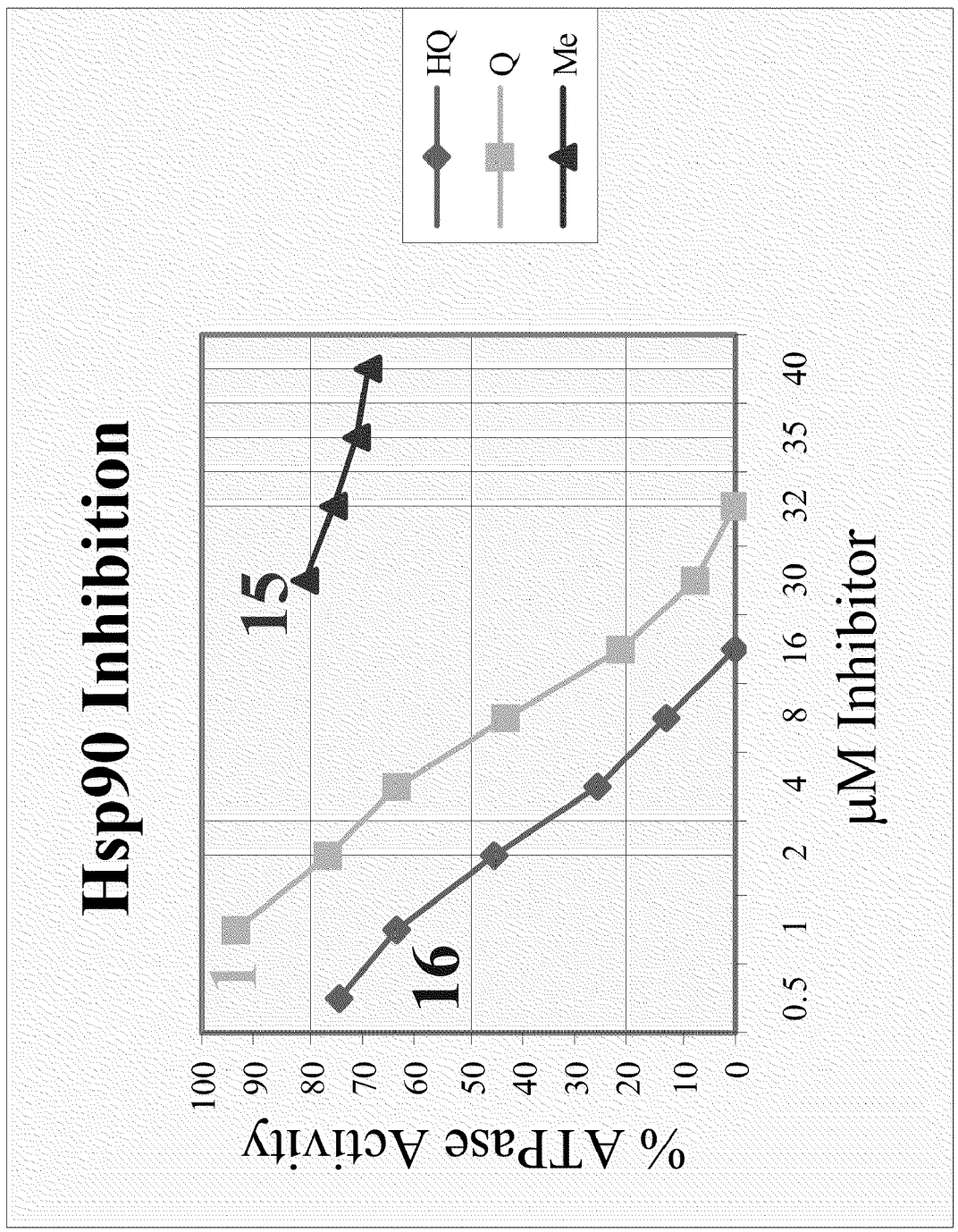
FIG. 4 graphically illustrates the inhibition of Hsp90's ATPase-activity with increasing concentrations of three seco-amide compounds of the present invention.

The pure protein was incubated with ATP and one of three RAD amides (the quinone, the 1,4-hydroxy, or the 1,4-methoxy), and the production of inorganic phosphate was determined. See Panaretou et al., *EMBO J.* 1998, 17, 4829-4836; Grenert et al., O. *J. Biol. Chem.* 1997, 38, 23843-23850; Chiosis, et al., *Mol. Cancer. Ther.* 2003, 2, 123-129; which are incorporated by reference in their entirety. These results are shown in FIG. 4.

wherein R is H or methyl.

The $IC_{50}$ of GDA as determined by this assay was consistent with previously reported values (2.5 μM) and the inhibitory activity of the quinone and the 1,4-hydroxy derivatives as 1.8 and 5.9 μM, respectively. See Agatsuma et al., *Bioorg. Med. Chem.* 2002, 10, 3445. The $IC_{50}$ of the 1,4-methoxy derivative was higher than 40 μM, suggesting the incorporation of methyl ethers onto the aromatic ring disrupts a key hydrogen bond network in the ATP binding pocket. Andrus and coworkers recently reported a similar result for the trimethoxy derivative of GDA, which resulted in a substantial loss in cellular efficacy (Andrus 2003).

| Compound | $IC_{50}$ (μm) |
| --- | --- |
| Quinone | 5.9 |
| 1,4-Methoxy | >40 |
| 1,4-Dihydroxy | 1.8 |
| Geldanamycin | 2.5 |

Figure 5:
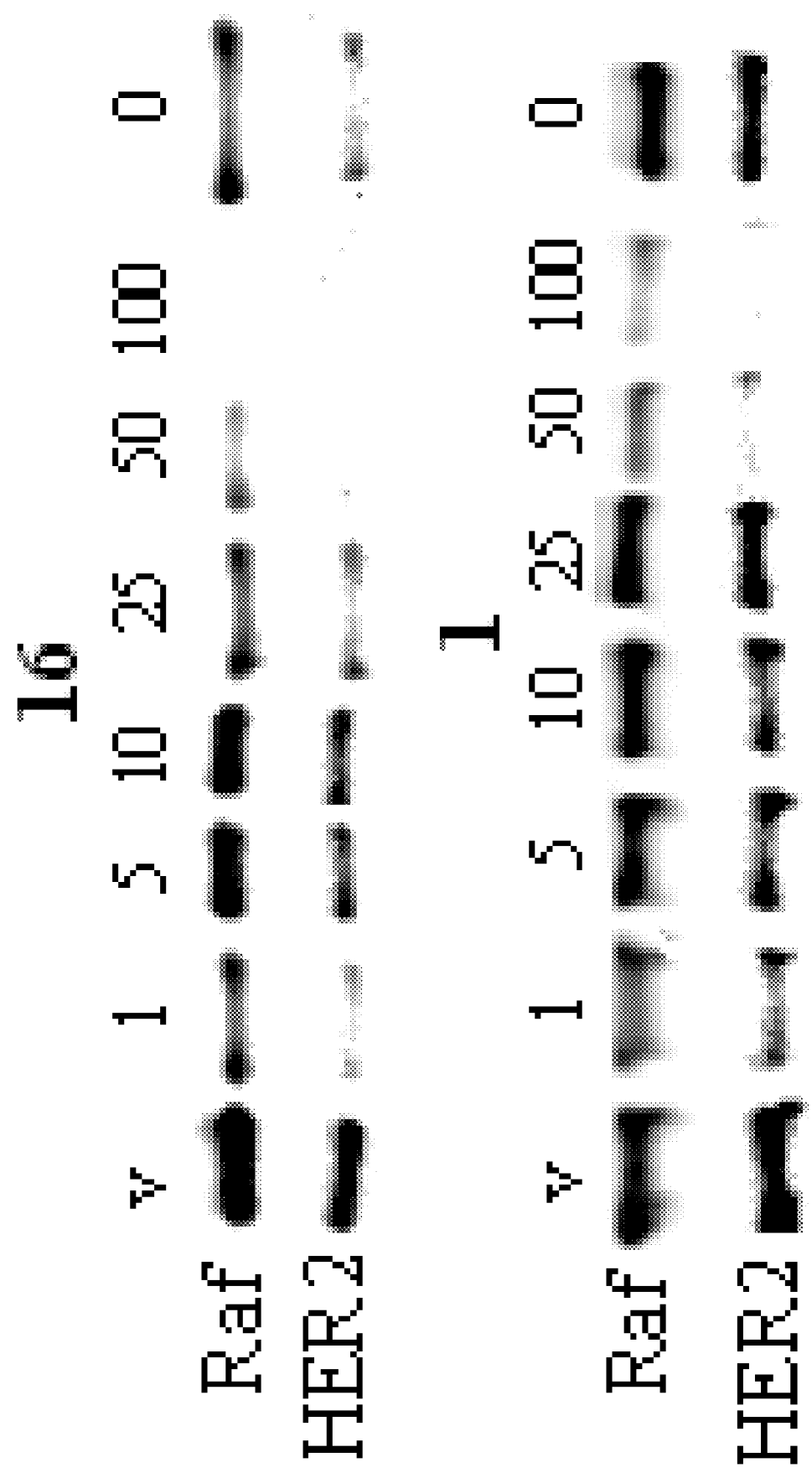
FIG. 5 is a Western Blot showing a concentration-dependent decrease in Hsp90 dependent client proteins, Raf and HER-2, with increasing concentrations of two seco-amide compounds in accordance with the present invention.

As mentioned previously, Hsp90 is responsible for the conformational maturation of several polypeptides into biologically active, three-dimensional structures. When the Hsp90 protein folding process is disrupted, these client proteins are unable to adopt their native structures, which ultimately leads to their degradation. Therefore, one can confirm Hsp90 inhibition by observing whether Hsp90 client proteins are degraded by analysis of cellular lysates in the presence of varying concentrations of Hsp90 inhibitors. As shown in FIG. 5, when increasing concentrations of the 1,4-hydroxy and quinone derivatives were incubated with MCF-7 breast cancer cells, a decrease in Hsp90-dependent client proteins, Raf and HER-2 were observed by Western Blot analysis, providing evidence that these molecules also inhibit Hsp90 in cells.

In addition, the following references, which are cited previously in the disclosure, are incorporated by reference in their entirety:

Andrus et al. Org. Let. 2003, 5, 3859-3862.

Andrus et al., *Total Synthesis of (+)-Geldanamycin and (−)-o-Quinogeldanamycin with Use of Asymmetric Anti- and Syn-Glycolate Aldol Reactions*, Org. Lett. 2002, 4, 3459-3452.

Andrus et al., J. Org. Chem.; (Article); 2003; 68(21); 8162-8169.

Barker et al., Addition of Silyloxydienes to 2,6-Dibromo-1,4-benzoquinone: An Approach to Highly Oxygenated Bromonaphtoquinones for the Synthesis of Thysanone. Tetranderon 2003, 59, 2441-2449.

Carpenter et al., *Reactions of the Carbanion from an Orsellinate Derivative with Electrophiles*, J. Chem. Soc. Perkin Trans. 1: Org. Biorg. Chem. 1984, 5, 1043-1051.

Chander & Chapman, Synthesis, 1988, 9, 743-745.

Charette et al., Asymmetric Cyclopropanations of Allylic Alcohols with Chiral Dioxaboralanes. J. Amer. Chem. Soc., 1994, 116, 2651-2652.

Crivello, J. V., *J. Org. Chem.* 1981, 46, 3056 (1998).

Fournier, J. P., Choay, P., Eur. Pat. Appl. No. EP006445 1982, 38 pp. entitled N-substituted 2,4-dialkoxybenzene Sulfone Amides.

Furstner et al., *Total Synthesis of Crystatic Acid*, Org. Lett. 2000, 2, 2467-70; Carpenter et al., *Reactions of the Carbanion from an Orsellinate Derivative with Electrophiles*, J. Chem. Soc. Perkin Trans. 1: Org. Biorg. Chem. 1984, 5, 1043-1051.

Gilman, H. et al., Dibenzofuran. XXI. Benzene and Biphenyl Intermediates for 1,9Derivatives, J. Am. Chem. Soc. 1944, 66, 858-859.

Hardegger et al., Wilting Agents and Antibiotics. XXXV. Structure of Diaporthin and the Synthesis of Diaporthinic Acid, Helv. Chim. Acta. 1966, 49, 1283-1290.

Hurd et al., Decarboxylation Studies on 3,5-Dihydroxyhomophtalic Acid Derivatives, J. Org. Chem. 1973, 38, 610-612.

Kraus et al., *Synthetic Studies toward Verrucarol*, Synthesis of the AB Ring System. J. Org. Chem. 1980, 45, 4825-4830.

Lampilas et al., Convergent Stereospecific Total Synthesis of Monocillin I and Monorden (or Radicicol), Tetrahedron 1992, 33, 777-780.

Luly et al., J. Org. Chem., 1984, 49, 1671-72.

Porwoll et al., Synthesis of [5,6-$^{13}C_2$, 1-$^{14}C$]Olivetolic Acid, Methyl [1'-$^{13}C$]Olivetolate and [5,6-$^{13}C_2$, 1-$^{14}C$]Cannabigerolic Acid, J. Labeled Compds. 1984, 22, 257-271.

Snyder et al., Oxidative Cleavage of Hydroquinone Ethers with Argentic Oxide, J. Am. Chem. Soc. 1972, 94, 227-231.

Yao et al., Kinetics of Liquid-phase Hydrogenation. III. The Nature of Platinum Oxide Catalysts, J. Am. Chem. Soc. 1961, 83, 799-801.

Yale, *Formylation of Amines with Phenyl Formate*, J. Org. Chem. 1971, 36, 3238-3240.

From the foregoing, it will be seen that this invention is one well adapted to attain all ends and objectives herein-above set forth, together with the other advantages which are obvious and which are inherent to the invention.

What is claimed and desired to be secured by Letters Patent is as follows:

1. Compound of the Formula III:

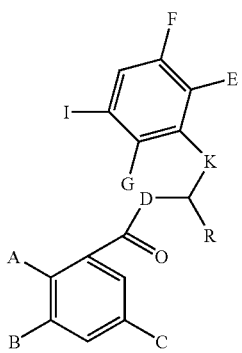

wherein A is hydrogen, halogen, lower alkyl, lower alkoxy, aryl, aralyl, allyl, or together with B and the atoms to which they are attached together form a heterocyclic ring having 4 to 12 ring members with at least one heteroatom selected from oxygen, nitrogen, or sulfur;

wherein B is hydroxy, amino, halogen, lower alkoxy, aralkoxy, or together with A and the atoms to which they are attached together form a heterocyclic ring having 4 to 12 ring members with at least one heteroatom selected from oxygen, nitrogen, or sulfur;

wherein C is hydroxy, amino, or lower alkoxy;

wherein D is alkyl, amino, oxygen, sulfanyl, sulfenyl, sulfonyl, or together with K and the carbon atoms to which they are attached form a carbocyclic ring or heterocyclic ring having 5 to 8 ring members; or D is alkyl and together with K and the carbon atoms to which they are attached form a carbocyclic ring or heterocyclic ring having 5 to 8 ring members;

wherein E is hydroxy, halogen, lower alkoxy, amino, allyl amine;

wherein F is hydroxy, halogen, thiol, lower alkoxy, amino, or is oxidized to form a ketone;

wherein G is hydrogen, hydroxy, halogen, amino, thiol, lower alkyl, lower alkoxy, or is oxidized to form a ketone;

wherein I is hydrogen, hydroxy, halogen, lower alkyl, lower alkoxy, thiol, amino, nitro, ester, or an amide comprising —NHCOR$_1$ and wherein is R$_1$ is hydrogen, lower alkyl, or lower alkoxy;

wherein K is alkyl, cycloalkyl, or together with D and the carbon atoms to which they are attached form a carbocyclic ring or heterocyclic ring having 5 to 8 ring members; and wherein R is hydrogen or alkyl.

2. The compound according to claim 1, corresponding to Formula III(A):

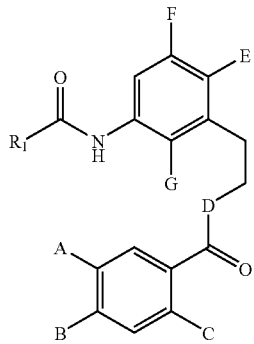

wherein A is hydrogen, chlorine, fluorine, methoxy, ethoxy, phenyl, benzyl, or allyl;
wherein B is hydroxy, chlorine, fluorine, methoxy, ethoxy, or benzoxy;
wherein C is hydroxy, amino, methoxy, or ethoxy;
wherein D is oxygen, alkyl, or —NH—;
wherein E is hydroxy, chlorine, fluorine, methoxy, ethoxy, or —NH$_2$;
wherein F is hydroxy, chlorine, fluorine, thiol, methoxy, ethoxy, amino, or is oxidized to form a ketone;
wherein G is hydroxy, chlorine, fluorine, —NH$_2$, thiol, methoxy, ethoxy, or is oxidized to form ketone; and
wherein R$_1$ is hydrogen, lower alkyl, or lower alkoxy.

3. The compound according to claim 1, corresponding to Formula III(C):

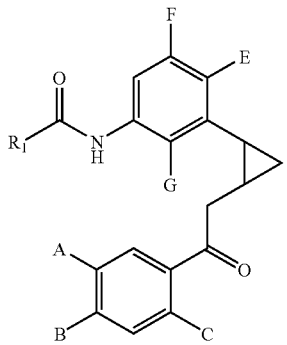

wherein A is hydrogen, chlorine, fluorine, methoxy, ethoxy, phenyl, benzyl, or allyl;
wherein B is hydroxy, chlorine, fluorine, methoxy, ethoxy, or benzoxy;
wherein C is hydroxy, amino, methoxy, or ethoxy;
wherein E is hydroxy, chlorine, fluorine, methoxy, ethoxy, or amino;
wherein F is hydroxy, chlorine, fluorine, thiol, methoxy, ethoxy, amino, or oxidized to form a ketone;
wherein G is hydroxy, chlorine, fluorine, thiol, methoxy, ethoxy, amino, or is oxidized to form a ketone; and
wherein is R$_1$ is hydrogen, lower alkyl, or lower alkoxy.

4. The compound according to claim 1, corresponding to Formula III(D):

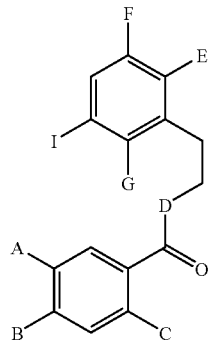

wherein A and B together with the atoms to which they are attached together form a heterocyclic ring having 4 to 10 ring members with at least one heteroatom selected from oxygen, nitrogen, or sulfur;
wherein C is hydroxy, amino, methoxy, or ethoxy;
wherein D is —CH$_2$—, —NH—, oxygen, sulfanyl, sulfenyl, or sulfonyl;
wherein E is chlorine, fluorine, hydroxy, methoxy, ethoxy, or amino;
wherein F is hydroxy, chlorine, fluorine, thiol, methoxy, ethoxy, amino, or is oxidized to from a ketone; and
wherein G is hydroxy, chlorine, fluorine, amino, thiol, methoxy, ethoxy, or is oxidized to form a ketone; and
wherein I is hydrogen, hydroxy, chlorine, fluorine, methyl, methoxy, ethoxy, or amino.

5. The compound according to claim 1, corresponding to Formula III(F):

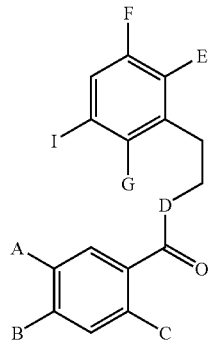

wherein A is hydrogen, chlorine, fluorine, methoxy, ethoxy, phenyl, benzyl, or allyl;
wherein B is hydroxy, chlorine, fluorine, methoxy, ethoxy, or benzoxy;
wherein C is hydroxy, amino, methoxy, or ethoxy;
wherein D is lower alkyl, oxygen, or —NH—;
wherein E is hydroxy, chlorine, fluorine, methoxy, ethoxy, or —NH$_2$;
wherein F is hydroxy, chlorine, fluorine, thiol, methoxy, ethoxy, amino, or is oxidized to form a ketone;
wherein G is hydroxy, chlorine, fluorine, amino, thiol, methoxy, ethoxy, or is oxidized to form a ketone; and
wherein I is hydrogen, hydroxy, chlorine, fluorine, methyl, methoxy, ethoxy, or amino.

6. The compound according to claim 1, corresponding to the Formula III:

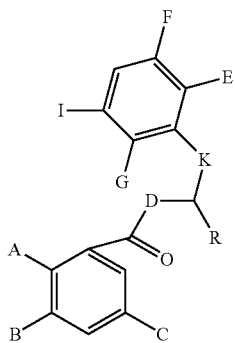

wherein A is hydrogen, halogen, lower alkyl, lower alkoxy, aryl, aralyl, allyl, or together with B and the atoms to which they are attached together form a heterocyclic ring having 4 to 12 ring members with at least one heteroatom selected from oxygen, nitrogen, or sulfur;
wherein B is hydroxy, amino, halogen, lower alkoxy, aralkoxy, or together with A and the atoms to which they are attached together form a heterocyclic ring having 4 to 12 ring members with at least one heteroatom selected from oxygen, nitrogen, or sulfur;
wherein C is hydroxy, amino, or lower alkoxy;
wherein D is alkyl, amino, oxygen, sulfanyl, sulfenyl, sulfonyl, or together with K and the carbon atoms to which they are attached form a carbocyclic ring or heterocyclic ring having 5 to 8 ring members; or D is alkyl and together with K and the carbon atoms to which they are attached form a carbocyclic ring or heterocyclic ring having 5 to 8 ring members;
wherein E is hydroxy, halogen, lower alkoxy, amino, allyl amine;
wherein F is hydroxy, or is oxidized to form a ketone;
wherein G is hydroxy, or is oxidized to form a ketone;
wherein I is hydrogen, hydroxy, halogen, lower alkyl, lower alkoxy, thiol, amino, ester, or an amide comprising —$NHCOR_1$ and wherein is $R_1$ is hydrogen, lower alkyl, or lower alkoxy;
wherein K is alkyl, cycloalkyl, or together with D and the carbon atoms to which they are attached form a carbocyclic ring or heterocyclic ring having 5 to 8 ring members; and
wherein R is hydrogen or alkyl.

7. The compound according to claim 6, wherein
A is halogen;
B is hydroxy;
C is hydroxy; and
D is oxygen.

8. The compound according to claim 7, wherein
I is an amide comprising —$NHCOR_1$ and wherein is $R_1$ is hydrogen, lower alkyl, or lower alkoxy.

9. The compound according to claim 8, wherein
E is lower alkoxy.

* * * * *